US006472392B1

(12) United States Patent
Starck et al.

(10) Patent No.: US 6,472,392 B1
(45) Date of Patent: Oct. 29, 2002

(54) TRIAZOLE COMPOUNDS AND THE USE THEREOF AS DOPAMINE-$D_3$ -LIGANDS

(75) Inventors: Dorothea Starck; Stefan Blank, both of Ludwigshafen; Hans-Jörg Treiber, Brühl; Liliane Unger, Ludwigshafen; Barbara Neumann-Schultz, Ladenburg; Theophile-Marie Le Bris, Bobenheim am Berg; Hans-Jürgen Teschendorf, Dudenhofen; Karsten Wicke, Altrip, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/446,520

(22) Filed: Dec. 28, 1999

(30) Foreign Application Priority Data

Jul. 7, 1997 (DE) .......................... 197 28 996

(51) Int. Cl.[7] .................. C07D 401/12; C07D 401/14; C07D 403/12; C07D 403/14; A61K 31/4196
(52) U.S. Cl. ............ 514/245; 514/252.11; 514/252.19; 514/253.05; 514/253.09; 514/242; 514/318; 514/326; 514/333; 514/340; 544/182; 544/198; 544/212; 544/328; 544/331; 544/363; 544/364; 544/366; 544/357; 546/194; 546/210
(58) Field of Search .............................. 544/327, 366, 544/198, 212, 364, 405; 546/210, 272.4; 540/575; 514/252.19, 254.05, 245, 253.09, 326, 340, 218; 548/236, 266.2, 266.8, 194, 253

(56) References Cited

U.S. PATENT DOCUMENTS

| | | | |
|---|---|---|---|
| 3,362,956 A | 1/1968 | Archer | 260/268 |
| 3,491,097 A | 1/1970 | Koppe et al. | 260/268 |
| 3,787,411 A | 1/1974 | Ruschig et al. | 260/268 |
| 3,839,336 A | 10/1974 | Borck et al. | 260/268 |
| 4,338,453 A | 7/1982 | Gall | 548/263 |
| 4,404,382 A | 9/1983 | Gall | 544/360 |
| 4,408,049 A | 10/1983 | Gall | 544/360 |
| 4,487,773 A | 12/1984 | Temple, Jr. et al. | 424/250 |
| 4,575,555 A | 3/1986 | Temple, Jr. et al. | 546/276 |
| 4,577,020 A | 3/1986 | Gall | 544/366 |
| 4,613,600 A | 9/1986 | Gammans et al. | 514/252 |
| 4,711,885 A | 12/1987 | Wierzbicki et al. | 514/253 |
| 4,784,998 A | 11/1988 | Yevich | 514/252 |
| 4,886,805 A | 12/1989 | Bru-Magniez et al. | 514/253 |
| 5,034,390 A | 7/1991 | Olsson et al. | 514/252 |
| 5,071,864 A | 12/1991 | Rendenbach-Mueller et al. | 514/370 |
| 5,075,308 A | 12/1991 | Ishikawa et al. | 514/252 |
| 5,256,664 A | 10/1993 | Mayol et al. | 514/252 |
| 5,292,739 A | 3/1994 | Merce-Vidal et al. | 514/253 |
| 5,322,846 A | 6/1994 | Jobard-Rouppert et al. | 514/252 |
| 5,346,896 A | 9/1994 | Ward et al. | 514/252 |
| 5,401,743 A | 3/1995 | Rendenbach-Mueller et al. | 514/252 |
| 5,401,762 A | 3/1995 | Rendenbach-Mueller et al. | 514/369 |
| 5,418,235 A | 5/1995 | Rendenbach-Mueller et al. | 514/252 |
| 5,688,795 A | 11/1997 | Pfister et al. | 514/252 |

FOREIGN PATENT DOCUMENTS

| | | |
|---|---|---|
| CA | 2195243 | 1/1996 |
| DE | 139082 | 2/1973 |
| DE | 139083 | 2/1973 |
| DE | 258033 | 5/1974 |
| DE | 4425143 | 1/1996 |
| DE | 4425144 | 1/1996 |
| DE | 4425145 | 1/1996 |
| DE | 4425146 | 1/1996 |
| GB | 1053085 | 12/1966 |
| WO | WO 92/07831 | 5/1992 |
| WO | WO 92/22541 | 12/1992 |
| WO | WO 97/25324 | 7/1997 |

OTHER PUBLICATIONS

J. Schwartz et al., "The Dopamine $D_3$ Receptor as a Target for Antipsychotics" Novel Antipsychotic Drugs (1992) pp. 134–144.

P. Sokoloff et al., "Localization and Function of the $D_3$ Dopamine Receptor" Forsch./Drug re. 42(1) Nr. 2a(1992) pp. 224–230.

P. Sololoff et al., "Molecular Cloning and Characterization of a Novel Dopamine Receptor ($D_3$) as a Target for Neuroleptics" Nature vol. 347 (1990) pp. 146–151.

Albright, "Reactions of Acyl Anion Equivalents Derived from Cyanohudrins, Protected Cyanohydrins and α–Dialkylaminonitriles" Tetrahedrdon vol. 39, No. 20 pp. 3207–3233, (1983).

D. Seebach, "Preparative Aspects of the Chemistry of 2–lithium–1,3dithianes and 2–lithium–1,3,5–triathianes are Surveyed. In Particular, Nucleophillic Acylation Reactions Using The Mentioned Lithium Derivatives" Synthesis, (1969) pp. 17–36.

(List continued on next page.)

Primary Examiner—Deepak R. Rao
(74) Attorney, Agent, or Firm—Keil & Weinkauf

(57) ABSTRACT

Triazole compounds of the following formula:

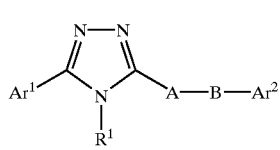

(I)

where $Ar^1$, A, B and $Ar^2$ have the meanings given in the description, possess a high affinity for the dopamine $D_3$ receptor and can therefore be used for treating diseases which respond to dopamine $D_3$ ligands.

14 Claims, No Drawings

OTHER PUBLICATIONS

D. Seebach, "Safe One–Pot Carbon–Carbon Bond Formation with Lithiated Nitrosamines Including Denitrosation by Sequential Reduction with Lithium Aluminum Hydride and Raney–Nickel" Synthesis, (1979) pp. 423–424.

Stetter, "Catalyzed Addition of Aldehydes to Activated Double Bonds—A New Synthetic Approach" Angewandte Chemie vol. 15, No. 11 (1976) pp. 639–712.

Van Niel et al., "Synthetic Uses of the 1,3 Dithiane Grouping from 1977 to 1988" Tetrahedron vol. 45 No. 24 (1989) pp. 7643–7677.

Martin et al. "Synthesis of Aldehydes, Ketones, and Carboxylic Acids from Lower Carbonyl Compounds by C–C Coupling Reactions" Synthesis (1979) pp. 633–665.

Kiristy et al. "Synthesis and Quantitative Structure–Activity Relationships of Some Antibacterial 3–Formylrifamycin SV N–(4–Substituted phenyl) piperazinoacethydrazones" Journal of Medicinal Chemistry vol. 21 No. 12 (1978) pp. 1301–1307.

C.B. Pollard "A New Synthesis of N–Monophenylpiperazine" J. Am. Chem. Soc. vol. 56 (1934) pp. 2199–2200.

S. Buchwald et al. Angew. Chem vol. 107 Nr. 12 (1995) pp. 1456–1459.

J. F. Hartwig et al. "A Second–Generation Catalyst for Aryl Halide Amination: Mixed Secondary Amines from Aryl Halides and Primary Amines Catalyzed by (DPPF)PdCl$_2$" J. Am. Chem Soc. vol. 118 (1996) pp. 7217–7218.

S. Buchwald et al. "Palldium–Catalyzed Amination of Aryl Triflates" J. Org. Chem. vol. 62 No. 5 (1997) pp. 1264–1267.

F. Kerrigan et al. "Synthesis of Arylpeperazines via Palladium–Catalysed Aromatic Amination Reactions of Bromoarenes with N–tert Butoxycarbonylpiperazine" Tetrahedron Letters No. 39 (1998) 2219–2222.

Stille, Angew. Chem vol. 98(1986) pp. 504–519.

Stille et al. "Palladium–Catalyzed Coupling of Allylic Acetates with Aryl–and Vinylstannanes" J. Org. Chem. vol. 55 No. 10 (1990) pp. 3019–3023.

Borjesson et al. "An Alternative Synthesis of Cyclic Aza Compounds" Acta Chemica Scandinavica vol. 45 (1991) pp. 621–626.

M. Majchrzak et al. Acya. Pol. Pharm. vol. 32 No. 2 (1975) pp. 145–148.

A. Yokoo et al. "Studies on Seven–membered Heterocyclic Compounds Containing Nitrogen. I. Synthesis of 1–Azacycloheptan–4–one Hydrochloride" Bull. Chem Soc. vol. 29 No. 5 (1956) pp. 631–632.

S. Kubota et al. "1,2,4–Triazoles. IV.[1)] Tautomerism of 3,5–Disubstituted 1,2,4–Triazoles" Chem Pharm. Bull. vol. 23 No. 5 (1975) pp. 955–966.

T. Kauffmann et al. "Synthesis and Properties of Azole–Pyridine Combinations: Problem of the Hydrolytic Cleavage of Hetarene Combinations" Angew. Chem. Intl. Ed. vol. 11 No. 9 (1972) pp. 846–847.

Rappoport et al. "Facile Introduction of Ester Groups into the Pyrrole Nucleus via Trichloroacetylation and Alcoholysis" J. Org. Chem. vol. 37 No. 23 (1972) pp. 3618–3622.

E. J. Browne "N–Unsubstituted–1,2,4–Triazole–3–Aldehydes" Tetrahedron Letters No. 12 (1970) pp. 943–944.

E. J. Browne "N–Unsubstituted 1,2,4–Triazole–3–Carbaldehydes" Aust. J. Chem. vol. 24 (1971) pp. 393–403.

E. J. Browne "Azole Aldehyde Condensations" Aust. J. Chem. vol. 26 (1973) pp. 1809–1814.

A. Czaranocka–Janowicz et al. "Synthesis and Pharmacological activity of 5–substituted–s–triazole–3–thiols" Pharmazie vol. 46 (1991) pp. 109–112.

Ohba et al. "Irreversible Inhibitions of Serine Proteases By Peptidyl Allylic Halide Derivatives" Biorganic & Medicinal Chemistry Letters vol. 6 No. 3 (1996) pp. 219–224.

Lowe et al. "1–Napthylpiperazine Derivatives as Potential Atypical Antipsychotic Agents" J. Med. Chem. vol. 34 No. 6 (1991) pp. 1860–1866.

TRIAZOLE COMPOUNDS AND THE USE THEREOF AS DOPAMINE-$D_3$-LIGANDS

This application is a 371 of PCT/EP98/04138 filed Jul. 3, 1998.

The present invention relates to triazole compounds and to the use of such compounds. The compounds mentioned have valuable therapeutic properties and can be used for treating diseases which respond to dopamine $D_3$ receptor ligands.

Compounds of this type having physiological activity have been disclosed. U.S. Pat. Nos. 4,338,453; 4,408,049 and 4,577,020 describe triazole compounds which have antiallergic or antipsychotic activity. DE-A 44 25 144 and WO 97/25324 describe triazole compounds which respond to dopamine $D_3$ receptor ligands. Compounds of the same structural type, however with other heterocycles in place of the triazole ring are disclosed in DE-A-44 25 146, DE-A-44 25 143 and DE 44 25 145.

Neurons obtain their information by way of G protein-coupled receptors, inter alia. A large number of substances exert their effect by way of these receptors. One of these substances is dopamine.

It is known with certainty that dopamine is present and that it has a physiological function as a neurotransmitter. Cells responding to dopamine are connected with the etiology of schizophrenia and Parkinson's disease. These and other diseases are treated with drugs which interact with the dopamine receptors.

Prior to 1990, two dopamine receptor subtypes were clearly defined pharmacologically, ie. the $D_1$ and $D_2$ receptors.

More recently, a third subtype has been found, ie. the $D_3$ receptor, which appears to mediate some of the effects of the antipsychotic drugs. (J. C. Schwartz et al., The Dopamine $D_3$ Receptor as a Target for Antipsychotics, in Novel Antipsychotic Drugs, H. Y. Meltzer, Ed. Raven Press, New York 1992, pages 135–144)

$D_3$ receptors are principally expressed in the limbic system. It is therefore assumed that a selective $D_3$ antagonist would probably have the antipsychotic properties of the $D_2$ antagonists but would not have their neurological side effects. (P. Solokoff et al., Localization and Function of the $D_3$ Dopamine Receptor, *Arzneim. Forsch./Drug Res.* 42(1), 224 (1992); P. Solokoff et al. Molecular Cloning and Characterization of a Novel Dopamine Receptor ($D_3$) as a Target for Neuroleptics, *Nature*, 347, 146 (1990)).

Surprisingly, it has now been found that certain triazole compounds exhibit a high affinity for the dopamine $D_3$ receptor and a low affinity for the $D_2$ receptor. These compounds are therefore selective $D_3$ ligands.

The present invention relates, therefore, to compounds of the formula I:

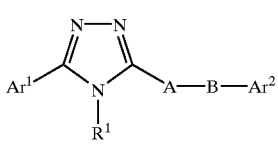

(I)

where

Ar$^1$ is phenyl, naphthyl or a 5- or 6-membered heterocyclic aromatic ring having from 1, 2, 3 or heteroatoms which are independently selected from O, S and N, where Ar$^1$ may have 1, 2, 3 or 4 substituents which are selected, independently of each other, from $C_1$–$C_6$-alkyl, which may be substituted by OH, $OC_1$–$C_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, $COOR^2$, $NR^2R^2$, $NO_2$, $SO_2R^2$, $SO_2NR^2R^2$, or phenyl, which may be substituted by $C_1$–$C_6$-alkyl, $OC_1$–$C_6$-alkyl, $NR^2R^2$, CN, $CF_3$, $CHF_2$, or halogen, and where the heterocyclic, aromatic ring mentioned may be fused to a phenyl ring;

A is straight-chain or branched $C_4$–$C_{10}$-alkylene or straight-chain or branched $C_3$–$C_{10}$-alkylene which comprises at least one group Z which is selected from O, S, NR$^2$, CONR$^2$, COO, CO, or a double or triple bond, B is a radical of the formula:

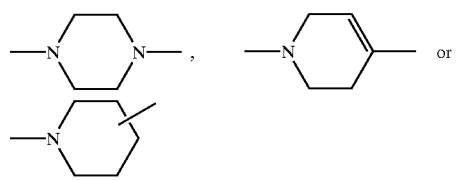

or, if Ar$^1$ represents the 5- or 6-membered, heterocyclic or aromatic ring which may be substituted as indicated, B may also be a radical of the formulae

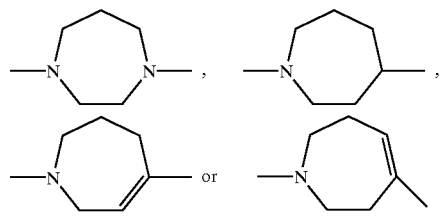

Ar$^2$ is phenyl, pyridyl, pyrimidinyl or triazinyl, where Ar$^2$ may have from 1 to 4 substituents which are selected, independently of each other, from $OR^2$, $C_1$–$C_6$ alkyl, $C_2$–$C_6$-alkenyl, $C_2$–$C_6$-alkynyl, $C_1$–$C_6$-alkoxy-$C_1$–$C_6$-alkyl, halogen-$C_1$–$C_6$-alkyl, halogen-$C_1$–$C_6$-alkoxy, halogen, CN, $NO_2$, $SO_2R^2$, $NR^2R^2$, $SO_2NR^2R^2$, a 5- or 6-membered carbocyclic, aromatic or non-aromatic ring and a 5- or 6-membered, heterocyclic aromatic or non-aromatic ring having 1 or 2 heteroatoms which are selected from O, S and N, where the carbocyclic or heterocyclic ring may be substituted by $C_1$–$C_6$-alkyl, phenyl, phenoxy, halogen, $OC_1$–$C_6$-alkyl, OH, $NO_2$ or $CF_3$ and where Ar$^2$ may be fused to a carbocyclic or heterocyclic ring of the above-defined nature, R$^1$ is H, $C_3$–$C_6$-cycloalkyl or $C_1$–$C_6$-alkyl which may be substituted by OH, $OC_1$–$C_6$-alkyl or phenyl;

the radicals R$^2$, which can be identical or different, are H or $C_1$–$C_6$-alkyl, which may be substituted by OH, $OC_1$–$C_6$-alkyl or phenyl;

and their salts with physiologically tolerated acids.

The novel compounds are selective dopamine $D_3$ receptor ligands which act in a regioselective manner in a limbic system and which, due to their low affinity for the $D_2$ receptor, have fewer side effects than the classic neuroleptics, which are $D_2$ receptor antagonists. The compounds can therefore be used for treating diseases which respond to dopamine $D_3$ receptor antagonists or dopamine $D_3$ receptor agonists, eg. for treating diseases of the central nervous system, in particular schizophrenia, depressions, neuroses, psychoses, parkinson and anxiety.

Within the context of the present invention, the following expressions have the meanings given in conjunction with them: Alkyl (also in radicals such as alkoxy, alkylamino, etc.) is a straight-chain or branched alkyl group having from 1 to 6 carbon atoms and, in particular, from 1 to 4 carbon atoms. The alkyl group can have one or more substituents which are selected, independently of each other, from OH, $OC_1$–$C_6$-alkyl, halogen or phenyl.

Examples of an alkyl group are methyl, ethyl, n-propyl, iso-propyl, n-butyl, iso-butyl, t-butyl, etc.

Cycloalkyl is, in particular, $C_3$–$C_6$-cycloalkyl, such as cyclopropyl, cyclobutyl, cyclopentyl and cyclohexyl.

Alkylene radicals are straight-chain or branched. If A does not have any group Z, A then comprises from 4 to 10 carbon atoms, preferably from 4 to 8 carbon atoms. The chain between the triazole nucleus and group B then has at least 4 carbon atoms. If A has at least one of said Z groups, A then comprises from 3 to 10 carbon atoms, preferably from 3 to 8 carbon atoms.

If the alkylene groups comprise at least one of the Z groups, these may either be arranged in the alkylene chain at an arbitrary site or in position 1 or 2 of group A (seen from the $Ar^1$ radical). The radicals $CONR^2$ and Coo are preferably arranged such that the carbonyl group is facing the triazole ring. Particularly preferred are compounds of the formula I in which A is —Z—$C_3$–$C_6$-alkylene, in particular —Z—$CH_2CH_2CH_2$—, —Z—$CH_2CH_2CH_2CH_2$—, —Z—$CH_2CH=CHCH_2$—, —Z—$CH_2C(CH_3)=CHCH_2$—, —Z—$CH_2C(=CH_2)CH_2$—, —Z—$CH_2CH(CH_3)CH_2$— or a linear —Z—$C_7$–$C_{10}$-alkylene radical, with Z being attached to the triazole ring. Z is preferably $CH_2$, O and in particular S. Further preferably is A —$(CH_2)_4$—, —$(CH_2)_5$—, —$CH_2CH_2CH=CHCH_2$—, —$CH_2CH_2C(CH_3)=CHCH_2$—, —$CH_2C(=CH_2)CH_2$—, or —$CH_2CH_2CH(CH_3)CH_2$—.

Halogen is F, Cl, Br or I.

Haloalkyl can comprise one or more, in particular 1, 2, 3 or 4, halogen atoms which can be located on one or more C atoms, preferably in the α- or ω-position. $CF_3$, $CHF_2$, $CF_2Cl$ or $CH_2F$ are particularly preferred.

Acyl is preferably HCO or $C_1$–$C_6$-alkyl-CO, in particular acetyl. When $Ar^1$ is substituted, the substituent can also be located on the nitrogen heteroatom.

Preferably, $Ar^1$ is

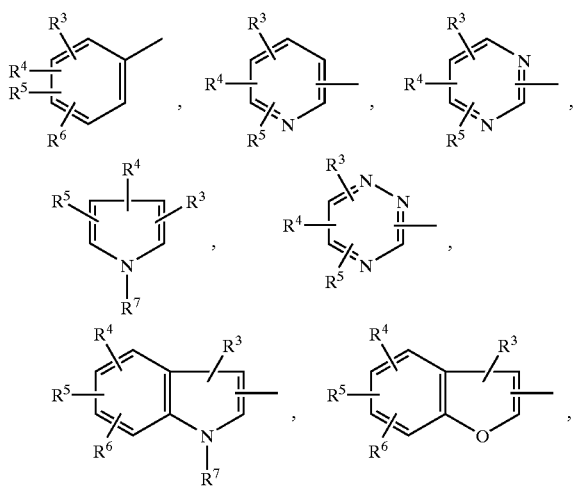

-continued

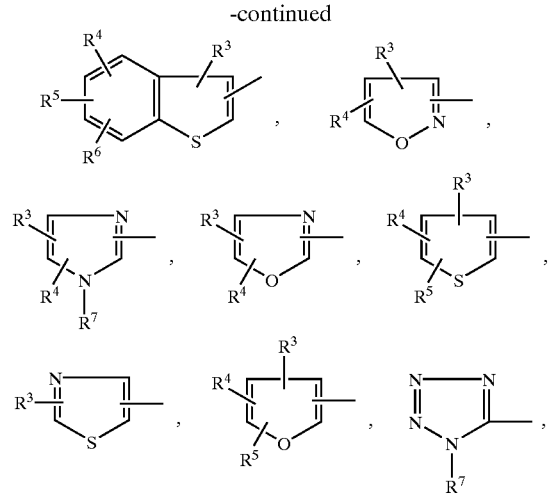

where
$R^3$ to $R^6$ are H or the abovementioned substituents of the radical $Ar^1$,
$R^7$ is H, $C_1$–$C_6$-alkyl or phenyl, and
X is N or CH. If the phenyl radical is substituted, the substituents are preferably in the m position or the p position.
Particularly preferably, $Ar^1$ is

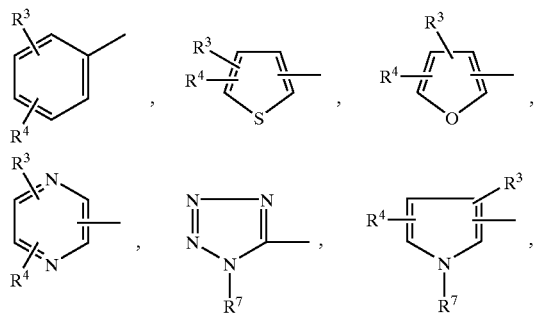

where $R^3$ and $R^4$ have the abovementioned meanings. The phenyl, pyrazinyl and pyrrole radicals which are indicated are particularly preferred.

The radicals $R^3$ to $R^6$ are preferably H, $C_1$–$C_6$-alkyl, $OR^2$, CN, phenyl which may be substituted by $C_1$–$C_6$-alkyl, $C_1$–$C_6$-alkoxy or halogen, $CF_3$ and halogen and, in particular, H, $C_1$–$C_6$-alkyl, $OR^2$ and halogen. In this context, $R^2$ has the abovementioned meanings.

The radical B is preferably

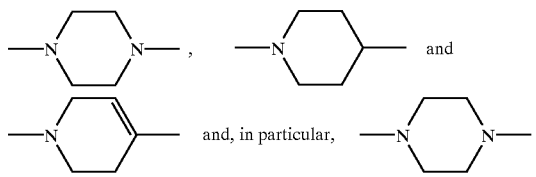

The radical $Ar^2$ may have one, two, three or four substituents, preferably one or two substituents, which are located, in particular, in the m position and/or the p position. They are preferably selected, independently of each other, from $C_1$–$C_6$-alkyl, haloalkyl, $NO_2$, halogen, in particular chlorine, phenyl, pyrrolyl, imidazolyl, pyrazolyl, thienyl, cyclopentyl and cyclohexyl. When one of the substituents is $C_1$–$C_6$-alkyl, a branched group and, in particular, isopropyl or t-butyl is preferred.

$Ar^2$ is preferably unsubstituted or substituted phenyl, 2-, 3- or 4-pyridinyl or 2-, 4(6)- or 5-pyrimidinyl.

When one of the substituents of the radical $Ar^2$ is a 5- or 6-membered heterocyclic ring, the ring is then, for example, a pyrrolidine, piperidine, morpholine, pyridine, pyrimidine, triazine, pyrrole, thiophene, or pyrazole radical, with a pyrrole, pyrrolidine, pyrazole or thienyl radical being preferred.

When one of the substituents of the $Ar^2$ radical is a carbocyclic radical, this latter radical is then, in particular, a phenyl, cyclopentyl or cyclohexyl radical.

When $Ar^2$ is fused to a carbocyclic radical, this latter radical is, in particular, a naphthalene or dihydro- or tetrahydro-naphthalene radical.

According to an embodiment the invention relates to compounds of formula I, wherein $Ar^1$ is a heterocyclic aromatic ring as defined above, B is

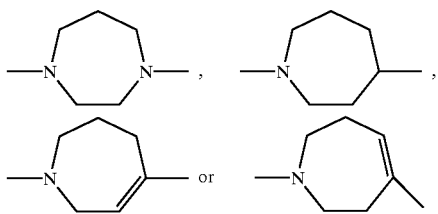

and A and Ar2 have the meanings given above.

The invention also encompasses the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other useful acids are described in Fortschritte der Arzneimittelforschung [Advances in drug research], Volume 10, pages 224 ff., Birkhäuser Verlag, Basle and Stuttgart, 1966.

The compounds of formula I can have one or more centers of asymmetry. The invention therefore also includes the relevant enantiomers and diastereomers in addition to the racemates. The respective tautomeric forms are also included in the invention.

The process for preparing the compound (I) comprises a) reacting a compound of the formula (II)

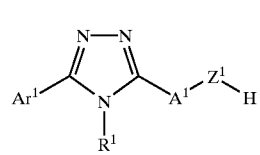

(II)

where $Y^1$ is a customary leaving group such as Hal, alkanesulfonyloxy, arylsulfonyloxy, etc., with a compound of the formula (III)

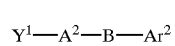

(III)

or b) reacting a compound of the formula (IV)

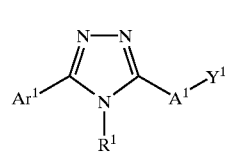

(IV)

where $Z^1$ is O, $NR^2$, or S and $A^1$ is $C_1$–$C_{10}$-alkylene or a bond, with a compound of the formula (V)

$Y^1$—$A^2$—B—$Ar^2$ (V)

where $Y^1$ has the abovementioned meaning and $A^2$ is $C_2$–$C_{10}$-alkylene, where $A^1$ and $A^2$ together have from 3 to 10 C atoms and $A^1$ and/or $A^2$ optionally comprises at least one group Z; or c) reacting a compound of the formula (VI)

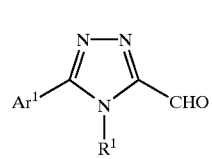

(VI)

where $Y^1$ and $A^1$ have the abovementioned meanings, with a compound of the formula (VII)

H—$Z^1$—A—B—$Ar^2$ (VII)

where $Z^1$ has the abovementioned meanings; or d) reversing the polarity of a compound of the formula (VIII)

(VIII)

using reagents which are known from the literature, such as 1,3-propanedithiol, KCN/water, TMSCN or KCN/morpholine, as described, for example, in Albright *Tetrahedron*, 1983, 39, 3207 or
D. Seebach *Synthesis* 1969, 17 and 1979, 19 or
H. Stetter *Angew. Chem. Int. Ed.* 1976, 15, 639 or
van Niel et al. *Tetrahedron* 1989, 45, 7643
Martin et al. *Synthesis* 1979, 633,
to give the products (VIIIa) (using 1,3-propanedithiol by way of example)

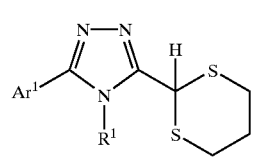

(VIIIa)

and then chain-elongating with compounds of the formula (IX)

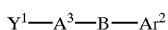
(IX)

where $Y^1$ has the abovementioned meanings and $A^3$ is $C_3$–$C_9$-alkylene, which may comprise a group Z
to give after deprotecting and reducing, compounds of the formula (Ia)

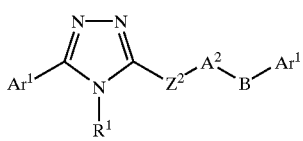
(Ia)

where $Z^2$ is CO, or a methylene group, and $Z^2$ and $A^2$ together have from 4 to 10 C atoms; or e) reacting a compound of the formula (VIII) with a compound of the formula X

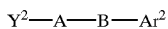
(X)

where $Y^2$ is a phosphorane or a phosphonic acid ester, by a method analogous to customary methods, as described, for example, in Houben weyl "Handbuch der Organischen Chemie" [Handbook of organic chemistry], 4th edition, Thieme Verlag Stuttgart, Volume 5/1b p. 383 ff. or Volume 5/1c p. 575 ff.

The process for preparing a compound of the formula I where A comprises the group COO or $CONR^2$ comprises in reacting a compound of the formula (XI)

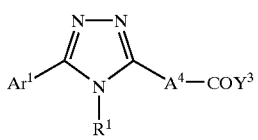
(XI)

where $Y^3$ is OH, $OC_1$–$C_4$, Cl or, together with CO, is an activated carboxyl group, and $A^4$ is $C_0$–$C_9$-alkylene, with a compound of the formula (XII)

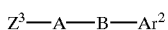
(XII)

where $Z^3$ is OH or $NH_2$.

The compounds of the formula (III) are starting compounds for preparing compounds of the formulae (V), (VII) and (XII), and are prepared by standard methods as described, for example, in J. A. Kiristy et al., J. Med. Chem. 1978, 21, 1303 or C. B. Pollard, J. Am. Chem. Soc. 1934, 56, 2199 or by a) reacting, in a known manner, a compound of the formula (XIII)

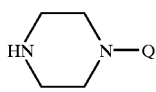
(XIII)

where Q is H or a customary amine protecting group, with a compound of the formula (XIV)

(XIV)

where $Y^4$ is $B(OH)_2$, —$SnR_3$ ($R^3$=butyl or phenyl), trifluoromethanesulfonyloxy, or has the meanings given for $Y^1$, and R is $C_1$–$C_4$-alkyl; or b) reacting a compound of the formula (XV)

(XV)

where $B^1$ is

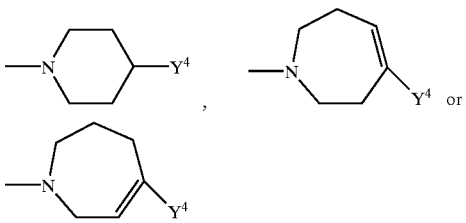

where Q is H or a customary amino protecting group, eg. butyloxycarbonyl, benzyl or methyl, and $Y^4$ is a leaving group, eg. OTf, $SnBu_3$, $B(OH)_2$ or halogen, with a compound of the formula (XIVa)

(XIVa)

where $Y^5$ is a boron derivative, such as $B(OH)_2$, or a metal-containing leaving group, for example $SnR_3$ ($R_3$=butyl or phenyl) or zinc halide, if $Y^4$ is halogen or trifluoromethylsulfonyloxy, or $Y^5$ is halogen or trifluoromethylsulfonyloxy, if $Y^4$ is a boron derivative, such as $B(OH)_2$, or a metal-containing leaving group, for example $SnR_3$ or zinc halide, as described in S. Buchwald et al. Angew. Chem. 1995, 107, 1456 or J. F. Hartwig et al. J. Am. Chem. Soc 1996, 118, 7217 or S. Buchwald J. Org. Chem. 1997, 62, 1264 or F. Kerrigan et al., Tetrah. Lett. 1998, 39, 2219 and the literature cited in that document, or J. K. Stille, Angew. Chem. 1986, 98, 504 or J. K. Stille et al. J. Org. Chem. 1990, 55, 3014 or M. Pereyre et al. "Tin in Organic Synthesis", Butterworth 1987; or c) reacting a compound of the formula (XVI)

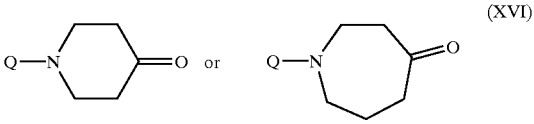
(XVI)

where Q has the abovementioned meanings, with a compound M—$Ar^2$, where M is a metal such as Li, or $MgY^6$, and $y^6$ is Br, Cl or I. M—$Ar^2$ can be obtained from compounds of the formula (XIV) using methods which are known from the literature, or d) preparing a compound of the formula (XVII)

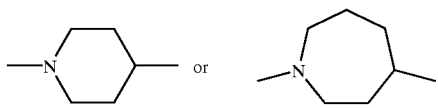
(XVII)

wherein B² is

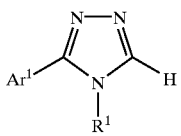

and Q has the abovementioned meaning, by reduction, for example hydrogenations of compounds of the general formula Q-B³-Ar² (IIIa), wherein B³ is one of the abovementioned unsaturated radicals B, using methods which are known from the literature.

Compounds of type B are either known or are obtained in a similar way to know methods as e.g. 1,4-diazacycloalkanes: L. Borjeson et al., Acta Chem. Scand. 1991, 45, 621; Majahrzahl et al. Acta. Pol. Pharm., 1975, 32, 145; 1-azacycloheptanones: A. Yokoo et al., Bull Chem. Soc. Jpn. 1956, 29, 631 and WO 97/25324.

In the above formulae, Ar¹, R¹, A, B, Z and Ar² are as defined above.

Compounds of the Ar¹-triazole, Ar₂, Ar¹ type are either known or can be prepared using known methods, as described, for example, in S. Kubota et al. Chem. Pharm. Bull 1975, 23, 955 or A. R. Katritzky, C. W. Rees(ed.) "Comprehensive Heterocyclic Chemistry", Pergamon Press, or "The Chemistry of Heterocyclic Compounds'" J. Wiley&Sons Inc. NY and the literature cited in that document.

The compounds of the formula VIII are novel and are likewise part of the subject-matter of the present invention.

Compounds of the (VIII) and (XI) type, where A is C₀-alkylene, can be prepared by metallating the 3-aryl-5-H-1,2,4(4H)-triazoles

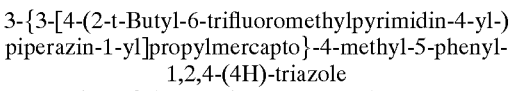

and by a method similar to methods described in T. Kauffman et al. Angew. Chem. Int. Ed. Engl. 1972, 11, 846 or by A. R. Katritzky, C. W. Rees(ed.) "Comprehensive Heterocyclic Chemistry", Pergamon Press Vol. 5, p 753.

The novel compounds and the starting materials and intermediates can also be prepared by a method similar to the methods described The above-described reactions generally take place in a solvent at between room temperature and the boiling temperature of the solvent employed. Examples of solvents which can be used are esters, such as ethyl acetate, ethers, such as diethyl ether or tetrahydrofuran, dimethylformamide, dimethyl sulfoxide, dimethoxyethane, toluene, xylene, ketones, such as acetone or methyl ethyl ketone, or alcohols, such as ethanol or butanol.

If desired, the reaction can be carried out in the presence of an acid binder. Suitable acid binders are inorganic bases, such as sodium or potassium carbonate, sodium or potassium hydrogen carbonate, sodium ethoxide or sodium hydride, or organometallic compounds, such butyllithium, or alkylmagnesium compounds, or organic bases, such as triethylamine or pyridine. The latter can simultaneously serve as solvents.

The reactions may be carried out using a catalyst, such as transition metals and their complexes, eg. Pd(PPh₃)₄, Pd(OAc)₂ or Pd(P(oTol)₃)₄, or using a phase transfer catalyst, eg. tetrabutylammonium chloride or tetrapropylammonium bromide.

The crude product is isolated in a customary manner, for example by filtering, by distilling off the solvent or by extracting from the reaction mixture, etc. The resulting compounds can be purified in a customary manner, for example by recrystallization from a solvent, by chromatography or by conversion into an acid addition compound.

The acid addition salts are prepared, in a customary manner, by mixing the free base with the appropriate acid, where appropriate in solution in an organic solvent, for example a lower alcohol, such as methanol, ethanol or propanol, an ether, such as methyl t-butyl ether, a ketone, such as acetone or methyl ethyl ketone, or an ester, such as ethyl acetate.

When used for treating the abovementioned diseases, the novel compounds are administered orally or parenterally (subcutaneously, intravenously, intramuscularly, or intraperitoneally) in a customary manner. They can also be administered through the nose/throat region using vapors or sprays.

The dose depends on the age, condition and weight of the patient and on the mode of administration. As a rule, the daily dose of active compound is from about 10 to 1000 mg per patient and day in the case of oral administration and from about 1 to 500 mg per patient and day in the case of parenteral administration.

The invention also relates to pharmaceuticals which comprise the novel compounds. These pharmaceuticals are present, in the customary pharmacological administration forms, in solid or liquid form, for example as tablets, film tablets, capsules, powders, granules, coated tablets, suppositories, solutions or sprays. In this context, the active compounds can be worked up together with the customary pharmacological auxiliary substances, such as tablet binders, fillers, preservatives, tablet disintegrants, flowance agents, emollients, wetting agents, dispersants, emulsifiers, solubilizers, retarding agents, antioxidants and/or propellant gases (cf. H. Sucker et al., Pharmazeutische Technologie [Pharmaceutical Technology], Thieme-Verlag, Stuttgart, 1978). The resulting administration forms normally comprise the active compound in a quantity of from 1 to 99% by weight.

The following examples serve to explain the invention without limiting it.

EXAMPLE 1

3-{3-[4-(2-t-Butyl-6-trifluoromethylpyrimidin-4-yl-)piperazin-1-yl]propylmercapto}-4-methyl-5-phenyl-1,2,4-(4H)-triazole A. Preparation of the Starting Compounds A.1 2-t-Butyl-4-[4-(3-chloropropyl)piperazin-1-yl]-6-trifluoromethylpyrimidine and 2,2-dimethylpropanimidamide were reacted, in a known manner, with ethyl trifluoroacetate to give 2-(2,2-dimethylethyl)-4-hydroxy-6-trifluoromethylpyrimidine. Heterocyclic Compounds (John Wiley & Sons, 1994, Vol. 52, D. J. Brown (Ed.)).

C₉H₁₁F₃N₂O m.p. 187–188° C.

A.2 After chlorinating with thionyl chloride, the crude product was treated with an excess of anhydrous piperazine, with 2-t-butyl-4-piperazin-1-yl-6-trifluoromethylpyrimidine being obtained.

C₁₃H₁₉F₃N₄ m.p. 78–80° C.

A.3 Alkylating the resulting compound with 1-bromo-3-chloropropane in tetrahydrofuran resulted in 2-t-butyl-4-[4-(2-chloropropyl)piperazin-1-yl]-6-trifluoromethylpyrimidine.

$C_{16}H_{24}ClF_3N_4$ m p. 83–84° C.

The inserted triazoles were obtained, if not stated otherwise, according to the method of S. Kubota et al., Chem Pharm Bull. 1975,23,955 by reacting the corresponding acid chlorides with alkyl thio semicarbazides in pyridine followed by cyclization in an aqueous solution of sodium hydrogencarbonate or by addition of the corresponding acid hydrazides with aklkyl thio isocyanates in a suitable solvent.

A.4 4-methyl-3-mercapto-5-(thiophen-3-yl-)1.2,4-(4H)-triazole

The sodium salt was isolated.

1H-NMR (DMSO-$d_6$): 3.7 (3H); 7.5 (m, 2H); 7.8 (m, 1H). mp: 146° C.

$C_7H_6N_3S_2Na$ (219)

A.5 4-methyl-3-mercapto-5-(2,5-dimethyl-furan-3-yl)-1,2,4-(4H)-triazole

1H-NMR (DMSO-$d_6$): δ=2.3 (s, 3H); 2.5 (s,3H); 3.7 (s, 3H); 6.1 (s, 1H).
28710/30

A.6 4-methyl-3-mercapto-5-(2,6-dichlor-phenyl)-1,2,4-(4H)-triazole

The sodium salt was isolated.

1H-NMR (DMSO-$d_6$): δ=3.7 (s, 3H); 7.4 (dd,1H); 7.6 (d, 1H); 8.2 (d, 1H).
mp: 220–225° C.

A.7 4-methyl-3-mercapto-5-(4-methylsulfony-phenyl) 1,2,4-(4H)-triazole

1H-NMR (DMSO-$d_6$): δ=3.7 (s, 3H); 7.4 (dd, 1H); 7.6 (d, 1H); 8.2 (d, 1H).
mp: 238–239° C.

A.8 4-methyl-3-mercapto-5-(3-bromopyridyl-5)-1,2,4-(4H)-triazole

The sodium salt was isolated.

1H-NMR (DMSO-$d_6$): δ=3.7 (s, 3H); 8.2(m,1H); 8.9 (m,2H).

A.9 4-methyl-3-mercapto-5-(pyrrol-2-yl)-1,2,4-(4H)-triazole

1H-NMR (DMSO-$d_6$): δ=3.7 (s, 3H); 6.2(m,1H); 6.8 (1,2H); 7.0 (m, 1H); 11.8 (s, 1H); 14.0 (s, 1H).
mp: 200–201° C.

A.10 4-methyl-3-mercapto-5-(3-benzthienyl)-1,2,4-(4H)-triazole

The sodium salt was isolated.

1H-NMR (DMSO-$d_6$): 3.8 (s, 3H); 7.5(m,2H); 8.0 (m,3H).

A.11 4-methyl-3-mercapto-5-(4-methyl-thiazol-5-yl)-1,2,4-(4H)-triazole

1H-NMR (DMSO-$d_6$): 2.4 (s,3H); 3.4 (s, 3H),9.2 (s,1H); 14.1 (s, 1H).

A.12 4-methyl-3-mercapto-5-(6-chlor-biphenyl-2)-1,2,4-(4H)-triazole

1H-NMR (DMSO-$d_6$): 3.8 (s, 3H), 7.6 (m, 1H), 7.9 (m, 1H); 8.1 (m, 3H); 8.4 (s, 1H).

A.13 4-methyl-3-mercapto-5-(2,4-dinitrophenyl-)-1,2,4-(4H)-triazole
mp: 250–251° C.
MS: m/z=281[M$^+$]

A.14 4-methyl-3-mercapto-5-(4-CF$_3$-phenyl) 1,2,4-(4H)-triazole
MS: m/z=259[M$^+$]

A.15 4-propyl-3-mercapto-5-(2-methyloxazol-4-yl)-1,2,4-(4H)-triazole

The potassium salt was isolated.

To a solution of 4.9 g (22.5 mmol) 2-methyloxazol-4-acidhydrazide-bishydrochloride (obtained by hydrazinolysis of the corresponding methyl ester in methanol solution) in 60 ml ethanol were successively added 6.22 g (95 mmol) potassium carbonate and 2.4 ml (23 mmol) propyl isothio cyanate and were 4 h heated to boiling.

The resulting suspension was filtered and concentrated and the residue (6.5 g) was purified by column chromatography (silica gel, methylene chloride-methanol 96:4). Yield: 2.3 g (39% of th.)

1H-NMR (CDCl$_3$): δ=1.0 (t, 3H); 1.7 (m,2H); 2.6 (s,3H); 4.2 (sm,2H); 8.1 (s,1H); 12.6 (s,1H).

A.16 4-propyl-3-mercapto-5-(2-amino-thiazol-4-yl) 1,2,4-(4H)-triazole

The potassium salt was isolated.

1H-NMR (DMSO-$d_6$): 0.8 (t,3H); 1.6 (m,2H); 3.4 (s, 2H); 4.3 (m,2H); 7.4 (s,1H); 13.8.

A.17 4-methyl-3-mercapto-5-(5-methylimidazol-4-yl) 1,2,4-(4H)-triazole

The potassium salt was isolated.

1H-NMR (DMSO-$d_6$): 2.3 (s,3H); 3.4 (s,3H); 7.5 (s,1H).

A.18 4-methyl-3-mercapto-5-(carboxamido) 1,2,4-(4H)-triazole

1H-NMR (DMSO-$d_6$): 3.7 (s,3H); 7.95 (s,1H); 8.25 (s,1H); 14.2 (s,1H).
MS: m/z=158[M$^+$]

A.19 4-methyl-3-mercapto-5-(N-methylpyrrol-2-yl)-1,2,4-(4H)-triazole 10.6 g (101.1 mmol) 4-methyl-3-thio semicarbazide and catalytic amounts of dimethyl amino pyridine were added to 10.2 g (45.1 mmol) 2-trichloracetoxy-N-methylpyrrol (obtained according to Rappoport et al., J. Org. Chem. 1972, 37, 3618) in DMF and heated to 90° C. for 18 h. 77 ml of water were added to the resulting product at room temperature, it as acidified with 10% HCl, stirred for 1 h at 0° C., filtered from the insoluble, and the original solution was extracted with ethyl acetate. The organic layers were dried, evaporated, and the resulting crude product was heated with a 427 ml solution of 1M sodium hydrogen carbonate to boiling. The original solution was filtered off the insoluble after completion of the reaction, was quenched and acidified with concentrated HCl, and the precipitated solid was isolated. Yield: 2.3 g (27% of th.)
MS: m/z=194 [M$^+$]

1H-NMR (DMSO-$d_6$): δ=3.6 (s,3H); 3.9 (s,3H); 6.2 (m,1H); 6.6 (m,1H); 7.1 (m,1H); 14.0 (1H).

B. Preparation of the End Product 576 mg (3 mmol) of 4-mercapto-3-methyl-5-phenyl-1,2,4-(4H)-triazole (prepared in accordance with the method of S. Kubota and M. Uda, Chem. Pharm. Bull. (1975), 23, 955–966 by reacting benzoyl chloride with N-methylthiosemicarbazide and subsequently cyclizing) and 1.1 g (3 mmol) of the chloropropyl compound described above under A.3 were heated, at 100° C. for 6 h, together with 7.2 mg (3 mmol) of lithium hydroxide in 10 ml of dry DMF while stirring. After the mixture had cooled down, 50 ml of water were added and the whole was extracted 3 times with t-butyl methyl ether. The organic phase was dried with sodium sulfate and concentrated by evaporation; the residue was purified by column chromatography (silica gel). The resulting pure substance (920 mg=59%) was subsequently converted into its hydrochloride using ethereal hydrochloric acid.

$C_{25}H_{33}ClF_3N_7S$ (556) m.p. 191–193° C.

The substances of the formula (I) which are listed in the following table were obtained in analogous manner.

TABLE 1

| Ex. | Ar¹ | R¹ | A | B | Ar² | Data |
|---|---|---|---|---|---|---|
| 1 | Phenyl | Me | —S(CH$_2$)$_3$— | Piperazinyl | 2-tert-butyl-4-methyl-6-(trifluoromethyl)pyrimidinyl | Hydrochloride m.p.: 191–193° C. |
| 2 | 2,4-Dimethoxyphenyl- | Me | —S(CH$_2$)$_3$— | Piperazinyl | 2-tert-butyl-4-methyl-6-(trifluoromethyl)pyrimidinyl | Hydrochloride m.p.: 154–157° C. |
| 3 | Phenyl | Me | —S(CH$_2$)$_3$— | Piperazinyl | 4-methyl-6-(trifluoromethyl)pyrimidinyl | m.p.: 91–93° C.; 1H-NMR(DMSO-d$_6$; ppm), 1.9(q, 2H); 2.45(m, 6H); 3.25(t, 2H); 3.6(s, 3H); 3.75(m, 4H); 7.25(s, 1H); 7.5(m, 3H); 7.8(m, 2H); 8.6(s, 1H). |
| 4 | 4-CN-Phenyl | Me | —S(CH$_2$)$_3$— | Piperazinyl | 2-tert-butyl-4-methyl-6-(trifluoromethyl)pyrimidinyl | Hydrochloride m.p.: 82° C. |
| 5 | Phenyl | Me | —S—CH$_2$—C(=CH$_2$)—CH$_2$— | Piperazinyl | 3-methyl-(OCF$_2$CHF$_2$)phenyl | 1H-NMR(CDCl$_3$; ppm): 2.55 (t, 4H); 3.18(s, 2H); 3.2(t, 4H); 4.0(s, 2H); 5.1(s, 1H); 5.2(s, 1H); 5.85(t, 1H); 6.7(m, 2H); 6.8(d, 1H); 7.2(d, 1H); 7.5(m, 3H); 7.7(m, 2H); |

TABLE 1-continued

| Ex. | Ar¹ | R¹ | A | B | Ar² | Data |
|---|---|---|---|---|---|---|
| 6 | Phenyl | Me | —S(CH₂)₃— | Piperazinyl | (pyrrolyl-pyrimidinyl-N-benzyl) | 1H-NMR(CDCl₃; ppm) 2.1(m, 2H); 2.5(m, 6H); 3.3 (t, 2H); 3.8(m, 7H); 4.5(d, 2H); 5.0(t, 1H); 5.2(s, 1H); 6.2(m, 2H); 7.3–7.4(m, 5H); 7.5(m, 3H); 7.6–7.7(m, 4H). |
| 7 | Phenyl | Me | —S(CH₂)₃— | Piperazinyl | (indolyl-methoxy-methyl-pyrimidinyl) | 1H-NMR(CDCl₃; ppm) 2.1(m, 2H); 2.5(m, 6H); 3.4(t, 2H); 3.6(s, 3H); 3.7(m, 4H); 4.1(s, 3H); 5.7(s, 1H); 6.6(d, 1H); 7.3(m, 2H); 7.5(m, 3H); 7.7(m, 3H); 8.2(d, 1H); 8.7(d, 1H). |
| 8 | 2-iodophenyl phenyl | Me | —S—CH₂—C(=CH₂)—CH₂— piperazinyl | | (t-butyl-methyl-trifluoromethyl-pyrimidinyl) | 1H-NMR(CDCl₃; ppm) 1.3(s, 9H); 2.6(m, 4H); 3.1 (s, 2H); 3.3(s, 3H); 3.7(m, 6H); 4.9(s, 1H); 5.1(s, 1H); 6.6(s, 1H); 7.2(t, 1H); 7.4(m, 1H); 7.6(s, 1H); 8.0(d, 1H). |

TABLE 1-continued

| Ex. | Ar¹ | R¹ | A | B | Ar² | Data |
|---|---|---|---|---|---|---|
| 9 | 4-Me-Phenyl | Me | —S(CH₂)₃— | Piperazinyl | 2-tBu-4-CF₃-6-Me-pyrimidinyl | 1H-NMR(CDCl₃; ppm) 1.3(s, 9H); 2.0(q, 2H); 2.5 (m, 6H); 3.3(t, 2H); 3.6(s, 3H); 3.7(m, 4H); 6.6(s, 1H); 7.3(d, 2H); 7.6(d, 2H); |
| 10 | 3-I-Phenyl | Me | —S(CH₂)₃— | Piperazinyl | 2-tBu-4-CF₃-6-Me-pyrimidinyl | 1H-NMR(CDCl₃; ppm) 1.3(s, 9H); 2.0(q, 2H); 2.4(s, 3H); 2.6(m, 6H); 3.4(t, 2H); 3.6(s, 3H); 3.8(m, 4H); 6.6(s 1H); 7.2(t, 1H); 7.6(d, 1H); 7.85(d, 1H); 8.0ss, 1H). |
| 11 | 2-Methoxy-phenyl | Me | —S(CH₂)₃— | Piperazinyl | 2,6-di-tBu-4-Me-pyrimidinyl | Fumarate m.p.: 77–80° C. |
| 12 | 2-Methoxy- | Me | —S(CH₂)₃— | Piperazinyl | 2-tBu-4-CF₃-6-Me-pyrimidinyl | Fumarate m.p.: 87–90° C. |

TABLE 1-continued

| Ex. | Ar¹ | R¹ | A | B | Ar² | Data |
|---|---|---|---|---|---|---|
| 13 | Phenyl | Me | —S(CH$_2$)$_3$— | Piperazinyl | 4-F-phenyl / 2-methyl-6-tert-butyl-pyrimidin-4-yl | 1H-NMR(CDCl$_3$; ppm) 1.4(s, 9H); 2.1(m, 2H); 2.6 (mbr, 6H); 3.4(t, 2H); 3.6(s, 3H); 3.7(mbr, 4H); 6.7(s, 1H); 7.1(d, 2H); 7.5(m, 3H); 7.6(m, 2H); 8.0(m, 2H); |
| 14 | 4-tert.-Butyl-phenyl | 3-Methoxy-prop-1-yl | —S(CH$_2$)$_3$— | piperazinyl | 2-tert-butyl-4-methyl-6-CF$_3$-pyrimidine | Hydrochloride m.p.: 102° C. |
| 15 | 4-tert.-Butyl-phenyl | Me | —S(CH$_2$)$_3$— | Piperazinyl | 2-tert-butyl-4-methyl-6-CF$_3$-pyrimidine | Hydrochloride m.p.: 155° C. |
| 16 | 2-I-Phenyl | Me | —S(CH$_2$)$_3$— | Piperazinyl | 2,4-di-tert-butyl-6-methyl-pyrimidine | 1H-NMR(CDCl$_3$; ppm) 1.3(s, 9H); 1.4(s, 9H); 2.1(q, 2H); 2.6(m, 6H); 3.4(m, 5H); 3.7(m, 4H); 6.3(s, 1H); 7.2(t, 1H); 7.4(d, 1H); 7.5(t, 1H); 7.9(d, 1H). |

TABLE 1-continued

| Ex. | Ar¹ | R¹ | A | B | Ar² | Data |
|---|---|---|---|---|---|---|
| 17 | 4-Methylphenyl | Me | —S(CH₂)₃— | Piperazinyl | 2,6-di-tert-butyl-4-methylpyrimidinyl | Hydrochloride m.p.: 156–160° C. |
| 18 | 4-Biphenyl | Me | —S(CH₂)₃— | Piperazinyl | 2,6-di-tert-butyl-4-methylpyrimidinyl | mp.164–165° C. |
| 19 | 3-I-Phenyl | Me | —S(CH₂)₃— | Piperazinyl | 2,6-di-tert-butyl-4-methylpyrimidinyl | Hydrochloride m.p.: 164–167° C. |
| 20 | Phenyl | Me | —O—(CH₂)₃— | Piperazinyl | 2-tert-butyl-4-methyl-6-trifluoromethylpyrimidinyl | 1H-NMR(CDCl₃; ppm) 1.3(s, 9H); 2.1(m, 2H); 2.6–2.8(m, 6H); 3.5(s, 3H); 3.8(mbr, 4H); 4.6(t, 2H); 6.5(s, 1H); 7.6(m, 3H); 7.8(m, 2H); |

TABLE 1-continued

| Ex. | Ar¹ | R¹ | A | B | Ar² | Data |
|---|---|---|---|---|---|---|
| 21 | Phenyl | Me | —CH=CH—CH₂—CH₂— | Piperazinyl | 2,6-di-tert-butyl-4-methylpyrimidinyl | m.p.: 156–161° C. 1H-NMR(CDCl₃; ppm) 1.3(s, 9H); 1.4(s, 9H); 2.6 (m, 8H); 3.7(m, 7H); 6.2(s, 1H); 6.4(d, 1H); 7.0(td, 1H); 7.5(m, 3H); 7.7(m, 2H). |
| 22 | Phenyl | Me | —(CH₂)₄— | Piperazinyl | 2,6-di-tert-butyl-4-methylpyrimidinyl | m.p.: 144–145° C. |
| 23 | Phenyl | Me | —(CH₂)₄— | Piperazinyl | 2-tert-butyl-4-trifluoromethyl-6-methylpyrimidinyl | 1H-NMR(CDCl₃; ppm) 1.3(s, 9H); 1.7(m, 2H); 1.9(q, 2H); 2.4(t, 2H); 2.5(t, 4H); 2.8(t, 2H); 3.6(s, 3H); 3.75(m, 4H); 6.6(s, 1H); 7.4(m, 3H); 7.6(m, 2H). |
| 24 | 2,5-dimethyl-3-furyl | Me | —S(CH₂)₃— | Piperazinyl | 2-tert-butyl-4-trifluoromethyl-6-methylpyrimidinyl | Hydrochloride m.p.: 190–192° C. |

TABLE 1-continued

| Ex. | Ar¹ | R¹ | A | B | Ar² | Data |
|---|---|---|---|---|---|---|
| 25 | Pyrazinylphenyl | Me | —S(CH$_2$)$_3$— | Piperazinyl | 2-tert-butyl-6-methyl-4-(trifluoromethyl)pyrimidinyl | Hydrochloride m.p.: 164° C. |
| 26 | Phenyl | Me | —S(CH$_2$)$_3$— | Piperazinyl | 4-methyl-6-[(1S)-1-phenylethylamino]-2-(pyrrol-1-yl)pyrimidinyl | 1H-NMR(CDCl$_3$; ppm) 1.5(d, 3H); 2.0(m, 2H); 2.4–2.6(m, 6H); 3.3(t, 2H); 3.6(m, 7H); 5.0–5.2(m, 2H); 5.8(s, 1H); 6.3(m, 2H); 7.2–7.4(m, 8H); 7.5(m, 3H); 7.6(m, 2H); |
| 27 | Phenyl | Me | —S(CH$_2$)$_3$— | Piperazinyl | 4-tert-butyl-2-methyl-6-(pyrrol-1-yl)pyrimidinyl | 1H-NMR(CDCl$_3$) 1.3(s, 9H); 2.1(m, 2H); 2.5 (m, 6H); 3.4(t, 2H); 3.6(s, 3H); 3.9(t, 4H); 6.3(m, 2H); 6.5 (s, 1H); 7.5(m, 5H); 7.6(m, 2H). |

TABLE 1-continued

| Ex. | Ar¹ | R¹ | A | B | Ar² | Data |
|---|---|---|---|---|---|---|
| 28 | 3-Thienyl | Me | —S(CH₂)₃— | Piperazinyl | 2-tert-butyl-6-methyl-4-CF₃-pyrimidinyl | 1H-NMR(CDCl₃; ppm) 1.3(s, 9H); 2.0(q, 2H); 2.5 (m, 6H); 3.3(t, 2H); 3.7(s, 3H); 3.75(m, 4H); 6.5(s, 1H); 7.5(m, 2H); 7.8(m, 1H). |
| 29 | 3-Thienyl | Me | —S—CH₂—C(=CH₂)—CH₂— | Piperazinyl | 2,4-di-tert-butyl-6-methyl-pyrimidinyl | 1H-NMR(CDCl₃; ppm) 1.3(s, 9H);1.4(s, 9H); 2.6(m, 4H); 3.1(s, 2H); 3.3(s, 3H); 3.7(m, 6H); 4.9(s, 1H); 5.1(s, 1H); 6.3(s, 1H); 7.5(m, 2H); 7.75(m, 1H); |
| 30 | 2,5-dimethyl-3-furyl | Me | —S—CH₂—C(=CH₂)—CH₂— | Piperazinyl | 2-isopropyl-6-methyl-4-CF₃-pyrimidinyl | 1H-NMR(CDCl₃) 1.2(s, 6H); 2.2(s, 3H); 2.4(s, 3H); 2.6(m, 4H); 2.9(m, 1H); 3.2(m, 2H); 3.5(br, 5H); 3.7(m, 4H); 3.9(s, 3H); 5.0(s, 1H); 5.15(s, 1H); 6.0(s, 1H); 6.5(s, 1H). |
| 31 | Phenyl | Me | —S(CH₂)₃— | Piperazinyl | 3,5-diisopropyl-methylphenyl | Fumarate m.p.: 146° C. |

TABLE 1-continued

| Ex. | Ar¹ | R¹ | A | B | Ar² | Data |
|---|---|---|---|---|---|---|
| 34 | 4-Methyl-phenyl | cProp | —S(CH₂)₃— | Piperazinyl | 5-chloro-4-trifluoromethyl-2-methylpyridin-yl | 1H-NMR(CDCl₃): 1.0(m, 4H); 2.0 (q, 2H); 2.4(s, 3H); 2.5(m, 6H); 2.8 (m, 1H); 3.7(mbr, 6H); 6.6(s, 1H); 6.7(s, 1H) 7.3(d, 2H); 7.6(d, 2H). |
| 32 | Phenyl | Me | —S(CH₂)₃— | Piperazinyl | 2-methyl-6-(furan-3-yl)pyrimidinyl | 1H-NMR(DMSO-d₆) Fumarat: 2.0 (m, 2H); 2.3(s, 3H); 2.7(m, 4H); 2.8 (m, 2H); 3.2(t, 2H); 3.6(s, 3H); 3.7 (m, 4H); 6.6(s, 1H); 6.7(m, 1H); 7.15(d, 1H); 7.5(m, 3H); 7.7(m, 2H); 7.9(m, 1H). |
| 33 | Phenyl | Me | —S—CH₂—C(=CH₂)—CH₂— | Piperazinyl | 3-methyl-1-pyrrolyl-phenyl | 1H-NMR(CDCl₃): 2.5(m, 4H); 3.1 (s, 2H); 3.3(m, 4H); 3.7(s, 2H); 5.1 (s, 1H); 5.2(s, 1H); 6.3(m, 2H); 6.7–6.9(m, 3H); 7.1(m, 2H); 7.4–7.7 (m, 6H). |
| 35 | Phenyl | iProp | —S(CH₂)₃— | 1-methyl-piperidin-4-yl | 3-trifluoromethyl-phenyl | 1H-NMR(DMSO-d₆) 1.5–2.0(m, 13H); 2.5(m, 4H); 2.7 (m, 2H); 3.4(m, 2H); 3.9(m, 1H); 7.5–7.7(m, 9H). |
| 36 | Phenyl | Me | —S(CH₂)₃— | 1-methyl-1,2,3,6-tetrahydropyridin-4-yl | 3-trifluoromethyl-phenyl | 1H-NMR(CDCl₃) 2.0(q, 2H); 2.5–2.7(m, 6H); 3.2(m, 2H); 3.5(t, 25H); 6-1(m, 1H); 7.3 (m, 3H); 7.4–7.7(m, 6H). |

TABLE 1-continued

| Ex. | Ar¹ | R¹ | A | B | Ar² | Data |
|---|---|---|---|---|---|---|
| 37 | Phenyl | nProp | —CONH—(CH₂)₄— | Piperazinyl | 2,6-di-tert-butyl-4-methylpyrimidinyl | 1H-NMR(CDCl₃) 1.0(t, 3H); 1.3(s, 9H); 1.4(s, 9H); 1.6–1.8(m, 6H); 2.6(m, 2H); 2.7 (m, 6H); 3.6(t, 2H); 3.8(m, 4H); 6.3 (s, 1H); 7.5(m, 3H); 7.7(m, 2H). |
| 38 | Phenyl | Me | —S(CH₂)₃— | Piperazinyl | 4-methylisoquinolinyl | 1H-NMR(CDCl₃) 2.05(q, 2H); 2.6(t, 2H); 2.7 (m, 4H); 3.2(m, 4H); 3.4(t, 2H); 3.6(s, 3H); 7.4–7.7 (m, 7H); 7.9(d, 1H); 8.1(d, 1H); 8.2(8s, 1H); 9.0(s, 1H). |
| 39 | N-methyl-2-pyrrolyl | Et | —S(CH₂)₃— | Piperazinyl | 2-methyl-6-(3-furyl)pyrimidinyl | 1H-NMR(DMSO-D₆) 1.8–2.0(m, 5H); 2.4(s, 3H); 2.5–2.7(m, 6H); 3.3(m, 2H); 3.7–3.8(m, 7H); 4.0(m, 2H); 6.2(s, 1H); 6.4(m, 1H); 6.6 (m, 3H); 6.9(m, 2H); 7.2 (s, 1H); 7.9(s, 1H). |
| 40 | 3,4-Dichlorophenyl | Me | —S(CH₂)₃— | 1,4-dimethyl-1,2,3,6-tetrahydropyridinyl | 3-(trifluoromethyl)phenyl | MS: m/z=473[M⁺] |
| 41 | 4-methylsulfonylphenyl | Me | —S(CH₂)₃— | Piperazinyl | 2-tert-butyl-4-(trifluoromethyl)-6-methylpyrimidinyl | m.p. 154° C. |

TABLE 1-continued

| Ex. | Ar¹ | R¹ | A | B | Ar² | Data |
|---|---|---|---|---|---|---|
| 42 | 4,5-dimethyl-imidazolyl (CH₃, CH₃, NH) | Propyl | —S(CH₂)₃— | Piperazinyl- | 2-tert-butyl-4-methyl-6-trifluoromethyl-pyrimidinyl | 1H-NMR(CDCl₃) 0.9(t, 3H); 1.3(s, 9H); 1.7 (m, 2H); 1.9(m, 2H); 2.3(s, 3H); 2.5(m, 6H); 3.3(m, 2H); 3.7 (m, 1H); 3.8(m, 4H); 4.3 (t, 2H); 6.7(s, 1H); 7.6(s, 1H). |
| 43 | Phenyl | Me | —S(CH₂)₈— | Piperazinyl- | 3-methylphenyl (CHF₂) | Hydrochloride m.p. 146° C. |
| 44 | Phenyl | Me | —S(CH₂)₆— | Piperazinyl- | 3-methylphenyl (CHF₂) | Hydrochloride m.p. 253° C. |
| 45 | 3-Bromopyridin-5-yl | Me | —S(CH₂)₃— | Piperazinyl | 2-tert-butyl-4-methyl-6-trifluoromethyl-pyrimidinyl | 1H-NMR(CDCl₃) 1.3(s, 9H); 2.1(m, 2H); 2.6 (m, 6H); 3.3(m, 3H); 3.7 (s, 1H); 3.8(m, 4H); 6.6(s, 1H); 8.2(s, 1H); 8.9(m, 2H). |
| 46 | 3-Thienyl | Me | —S(CH₂)₃— | Piperazinyl | 2-tert-butyl-4-methyl-6-propyl-pyrimidinyl | 1H-NMR(CDCl₃) 1.0(t, 3H); 1.3(s, 9H); 1.7 (m, 2H); 1.9(m, 2H); 2.6 (m, 8H); 3.4(t, 2H); 3.7 (m, 7H); 6.2(s, 1H); 7.5 (m, 2H); 7.7(s, 1H). |

TABLE 1-continued

| Ex. | Ar¹ | R¹ | A | B | Ar² | Data |
|---|---|---|---|---|---|---|
| 47 | 4-tert.-Butyl-phenyl- | Me | —S—CH₂—C(CH₃)=CH₂— | Piperazinyl | 2-tert-butyl-6-methyl-4-CF₃-pyrimidinyl | 1H-NMR(CDCl₃) 1.4(2s, 18H); 1.9(s, 3H); 2.5 (t, 4H); 3.0(d, 2H); 3.7(m, 7H); 3.9(s, 2H); 5.5(t, 1H); 6.5 (s, 1H); 7.5(d, 2H); 7.6(d, 2H); |
| 48 | Phenyl | Propyl | —S(CH₂)₃— | Piperazinyl | 2,4-di-tert-butyl-6-methyl-pyridinyl | 1H-NMR(CDCl₃) 1.3(s, 9H); 1.4(s, 9H); 2.0 (m, 2H); 2.6(m, 6H); 3.3 (t, 3H); 3.6(m, 7H); 6.4(s, 1H); 6.7(s, 1H); 7.4(m, 3H); 7.7 (m, 2H); |
| 49 | 2-amino-4-methyl-thiazolyl | Propyl | —S(CH₂)₃— | Piperazinyl | 2-tert-butyl-6-methyl-4-CF₃-pyrimidinyl | 1H-NMR(CDCl₃) 0.9(t, 3H); 1.3(s, 9H); 1.7 (m, 2H); 2.0(q, 2H); 2.5 (m, 6H); 3.3(t, 3H); 3.7 (mbr, 2H); 4.3(t, 2H); 6.2 (s, 1H); 8.9(s, 1H); |
| 50 | 2-Benzthienyl | Me | —S(CH₂)₃— | Piperazinyl | 2-tert-butyl-6-methyl-4-CF₃-pyrimidinyl | m.p. 143° C. |

TABLE 1-continued

| Ex. | Ar¹ | R¹ | A | B | Ar² | Data |
|---|---|---|---|---|---|---|
| 51 | 2-methyl-3-methylthiazole (CH₃ at 3, CH₃ at 2, S, N) | Me | —S—CH₂—C(=CH₂)—CH₂— | Piperazinyl | 2-isopropyl-6-tert-butyl-4-methylpyrimidine | 1H-NMR(CDCl₃) 1.2(d, 6H); 1.4(s, 9H); 2.5 (m, 7H); 2.9–3.0(m, 3H); 3.5 (s, 3H); 3.8(s, 2H); 5.0(s, 1H); 5.2(s, 1H); 6.2(s, 1H); 8.9 (s, 1H). |
| 52 | 5-methyl-1H-1,2,4-triazole | Me | —S—CH₂—C(=CH₂)—CH₂— | Piperazinyl | 2-tert-butyl-4-CF₃-6-methylpyrimidine | m.p. 150° C. |
| 53 | Phenyl | n-Propyl | —CO—(CH₂)₃— | Piperazinyl | 2-tert-butyl-4-propyl-6-methylpyrimidine | Bishydrochloride 1H-NMR(DMSO-d₆) 1.0(t, 3H); 1.5(s, 9H); 1.7 (m, 2H) 2.2(m, 2H); 3.0 (t, 2H); 3.3(m, 4H); 3.4 (m, 2H); 3.7(m, 3H); 3.9 (m, 4H); 4.5(m, 1H); 5.0 (m, 1H); 7.2(s, 1H); 7.6 (m, 3H); 7.8(m, 2H). |
| 54 | 6-chloro-2-methylnaphthalene | Me | —S(CH₂)₃— | Piperazinyl | 2-tert-butyl-4-CF₃-6-methylpyrimidine | Hydrochloride m.p. 150° C. MS: m/z=641[M⁺] |

TABLE 1-continued

| Ex. | Ar¹ | R¹ | A | B | Ar² | Data |
|---|---|---|---|---|---|---|
| 55 | 4-methyl-2-methyl-oxazolyl | Propyl | —S(CH₂)₃— | Piperazinyl | 2-tert-butyl-4-methyl-6-CF₃-pyrimidinyl | 1H-NMR(CDCl₃) 0.9(t, 3H); 1.3(s, 9H); 1.7 (m, 3H); 1.9(q, 2H); 2.6 (m, 9H); 3.3(t, 2H); 3.7 (m, 4H); 4.3(t, 2H); 6.6(s, 1H); 8.2(s, 1H). |
| 56 | 2-Pyrrolyl | Me | —S(CH₂)₃— | Piperazinyl | 2-tert-butyl-4-methyl-6-propyl-pyrimidinyl | 1H-NMR(CDCl₃): 1.0(t, 3H); 1.3(s, 9H); 1.7 (m, 2H); 2.0(m, 3H); 2.5 (m, 8H); 3.3(t, 2H); 3.6(t, 4H); 3.8(s, 3H); 6.2(s, 1H); 6.3 (m, 1H); 6.6(m, 1H); 7.1 (m, 1H). |
| 57 | 3-methyl-2,5-dimethyl-furyl | Me | —S—CH₂—C(=CH₂)—CH₂— | 1,4-dimethyl-diazepanyl | 2-tert-butyl-4-methyl-6-CF₃-pyrimidinyl | Hydrochloride m.p. 116° C. |
| 58 | 4-methyl-2-methyl-oxazolyl | Propyl | —S—CH₂—C(=CH₂)—CH₂— | 1,4-dimethyl-diazepanyl | 2-tert-butyl-4-methyl-6-CF₃-pyrimidinyl | Hydrochloride m.p.: 76° C. MS: m/z=525[M⁺] |

TABLE 1-continued
| Ex. | Ar¹ | R¹ | A | B | Ar² | Data |
|---|---|---|---|---|---|---|
| 59 | 4-Ethinylphenyl | Me | —S(CH₂)₃— | Piperazinyl |  | MS: m/z=532[M⁺] |
| 60 | 3-Thienyl | Me | —(CH₂)₄— | 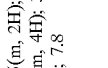 |  | 1H-NMR(CDCl₃): 1.7–1.9(m, 4H); 2.5–2.7 (m, 2H); 2.9(t, 2H); 3.2 (m, 2H); 3.7(s, 3H); 7.3–7.5 (m, 6H); 7.8(m, 1H). MS: m/z=395[M⁺] |
| 61 | 3-Thienyl | Me | —(CH₂)₄— | 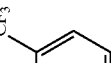 | 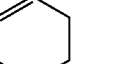 | 1H-NMR(CDCl₃): 1.7–2.0(m, 8H); 2.5(m, 2H); 2.9(t, 2H); 3.1–3.3(m, 4H); 3.7 (s, 3H); 7.5(m, 2H); 7.8 (m, 1H). MS: m/z=393[M⁺] |
| 62 | 3,4-Dichlorophenyl | Me | —(CH₂)₄— | Piperazinyl |  | 1H-NMR(CDCl₃): 1.3(s, 9H); 1.4(s, 9H); 1.7 (m, 2H); 1.9(m, 2H); 2.5 (m, 6H); 2.9(t, 2H); 3.6–3.8 (m, 7H); 6.2(s, 1H); 7.4(dd, 1H); 7.6(d, 1H); 8.2(d, 1H). |
| 63 | N-Methyl-2-pyrrolyl | Et | —(CH₂)₄— | Piperazinyl | | 1H-NMR(CDCl₃): 1.3(s, 9H); 1.7–2.0(m, 6H); 2.5(m, 6H); 2.9(t, 2H); 3.7–4.1 (9H); 6.2(s, 1H); 6.4(m, 1H); 6.6(s, 1H); 6.8(m, 1H). |

TABLE 1-continued

| Ex. | Ar¹ | R¹ | A | B | Ar² | Data |
|---|---|---|---|---|---|---|
| 64 | 3-Bromopyridin-5-yl | cProp | —S(CH₂)₃— | Piperazinyl | 2-tBu-4-CF₃-6-Me-pyrimidinyl | 1H-NMR(CDCl₃) 1.0(m, 4H); 1.3(s, 9H); 2.1 (m, 2H); 2.8(m, 1H); 3.6 (m, 6H); 3.3(m, 3H); 3.8 (m, 4H); 6.6(s, 1H); 8.2(s, 1H); 8.9(m, 2H). |
| 65 | 5-methyl-1H-tetrazol-yl | Me | —S(CH₂)₃— | Piperazinyl | 2-tBu-4-CF₃-6-Me-pyrimidinyl | m.p. 133° C. |
| 66 | 4-CF₃-Phenyl | Me | —S(CH₂)₃— | Piperazinyl | 2,4-di-tBu-6-Me-pyrimidinyl | MS: m/z=576[M⁺] |
| 67 | Pyrazinyl | Me | —S(CH₂)₃— | 4-methyl-1,4-diazepan-1-yl | 2,4-di-tBu-6-Me-pyrimidinyl | Hydrochloride m.p. 131° C. MS: m/z=524[M⁺] |

TABLE 1-continued

| Ex. | Ar$^1$ | R$^1$ | A | B | Ar$^2$ | Data |
|---|---|---|---|---|---|---|
| 68 | 2,4-Dinitrophenyl | Me | —S(CH$_2$)$_3$— | Piperazinyl | 2,6-di-tert-butyl-4-methylpyrimidinyl | 1H-NMR(CDCl$_3$) 1.3(s, 9H); 1.4(s, 9H); 2.0 (m, 2H); 2.6(m, 6H); 3.3 (t, 3H); 3.8(mbr, 7H); 6.2 (s, 1H); 7.8(d1H); 8.6(dd, 1H); 9.1(d, 1H). |
| 69 | 4,5-dimethyl-1H-imidazolyl | Me | —S(CH$_2$)$_3$— | 1,4-dimethyl-[1,4]diazepanyl | 2-tert-butyl-4-methyl-6-trifluoromethylpyrimidinyl | 1H-NMR(CDCl$_3$) 1.3(s, 9H); 1.9(m, 4H); 2.3(s, 3H); 2.6(m, 4H) 2.8(m, 2H); 3.3(t, 2H); 3.5(mbr, 2H); 3.8 (s, 3H); 3.9–4.1(m, 2H); 6.6 (s, 1H); 7.6(s, 1H); 12.8 (br, 1H). |
| 70 | 5-bromo-3-methylpyridinyl | Me | —S(CH$_2$)$_3$— | 1,4-dimethyl-[1,4]diazepanyl | 2-tert-butyl-4-methyl-6-trifluoromethylpyrimidinyl | 1H-NMR(CDCl$_3$) 1.3(s, 9H); 2.0(m, 4H); 2.3(s, 3H); 2.6(m, 4H); 2.8(m, 2H); 3.3(t, 2H); 3.6(m, 2H); 3.7 (s, 3H); 4.1(m, 2H); 6.6(s, 1H); 8.2(m, 1H); 8.8(m, 2H). |
| 71 | 5-methyl-1H-1,2,4-triazolyl | Me | —S(CH$_2$)$_3$— | 1,4-dimethyl-[1,4]diazepanyl | 2-tert-butyl-4-methyl-6-trifluoromethylpyrimidinyl | 1H-NMR(CDCl$_3$) 1.3(s, 9H); 1.8–2.1(m, 4H), 2.6–2.9(m, 6H); 3.1(m, 2H); 3.6(mbr, 2H); 3.8–4.1(m, 5H); 6.6(s, 1H). | c = cyclo, for example cProp = cyclopropyl

EXAMPLE 20

3-{3-[4-(2-t-Butyl-6-trifluoromethylpyrimidin-4-yl)piperazin-1-yl]propoxy}-4-methyl-5-phenyl-1,2,4-(4H)-triazole 855 mg (3mmol) of 3-iodo-4-methyl-5-phenyl-1,2,4-(4H)-triazole (prepared by iodinating 4-methyl-5-phenyl-1,2,4-(4H)-triazole by a method similar to Izv. Akad. Nauk SSSR, Ser. Khim (1975), 616–619), were stirred, at 60° C. for 6 h, with 1.04 g (3 mmol) of 2-t-butyl-4-[4-(3-hydroxypropyl)piperazin-1-yl]-6-trifluoromethyl pyrimidine (prepared, by a method similar to Example 1, A.3, by reacting the product obtained as described in Example 1, A.2 with 3-chloropropanol) and sodium hydride in DMF. For the working-up, ice water was added to the mixture and the whole was extracted several times with methyl t-butyl ether. The residue which was obtained after drying with sodium sulfate and removing the solvent was purified by column chromatography (silica gel, methylene chloride/methanol). Yield, 140 mg (9% of theory) of oil.

$C_{25}H_{32}F_3N_7O$ (503)

1H NMR (CDCl$_3$): 1.3 (s,9H); 2.1 (m,2H); 2.6–2.8 (m,6H); 3.5 (s,3H); 3.8 (mbr,4H); 4.6 (t,2H); 6.5 (s,1H); 7.6 (m,3H); 7.8 (m,2H);

EXAMPLE 21

3-{4-[4-(2,6-Di-t-butylpyrimidin-4-yl)piperazin-1-yl]but-1-enyl}-4-methyl-5-phenyl-1,2,4-(4H)-triazole a. 3-Formyl-4-methyl-5-phenyl-1,2,4-(4H)-triazole 18.5 g (116 mmol) of 4-methyl-5-phenyl-1,2,4-(4H)-triazole were dissolved in 235 ml of absolute THF and the solution was cooled down to −70° C.; 85 ml (139 mmol) of a 15% strength solution of butyllithium in hexane were then added at this temperature over the course of 15 min. After 45 min, 72 ml (1.16 mmol) of methyl formate were added over the space of 5 min, in association with which the temperature rose to −50° C. The mixture was subsequently stirred for a further 2 h at −50 to −70° C. and for 30 min at −25° C.; solid ammonium chloride was then added, after which ice water was added and the whole was extracted 3 times with methylene chloride. After drying and evaporating off the solvent, 22.8 g of residue remained, which residue was purified by means of flash chromatography (silica gel, ethyl acetate/methanol).

Yield: 10.9 g (46% of theory)

$C_{10}H_9N_3O$ (187)

1H NMR (CDCl$_3$): 3.9 (s,3H); 7.6 (m,3H); 7.7 (m,2H); 10.2 (s,1H).

b. 3-[4-(2,6-Di-t-butylpyrimidin-4-yl)piperazin-1-yl]propyl-triphenylphosphonium chloride 3.52 g (10 mmol) of 1-chloro-3-[4-(2,6-di-t-butylpyrimidin-4-yl)piperazin-1-yl]propane (prepared by a method similar to Example 1, A.3) were dissolved, together with 1.8 g of sodium iodide (12 mmol) and 3.41 g (13 mmol) of triphenylphosphine in 75 ml of acetone and the solution was refluxed for 24 h.

After the mixture had been cooled down, the precipitate was filtered off with suction, the filtrate was concentrated by evaporation under reduced pressure and the residue was purified by column chromatography (silica gel, methylene chloride containing 3.5% methanol). Yield: 6.25 g (88% of theory).

$C_{37}H_{48}IN_4P$ (706).

1H NMR (CDCl$_3$): 1.3 (s,9H); 1.4 (s,9H); 1.9 (m,2H); 2.4 (m,4H); 2.7 (m,2H); 3.6 (m,4H); 3.9 (mbr, 2H); 6.3 (s,1H); 7.6–7.9 (m,15H).

c. 5.88 g (8.3 mmol) of the phosphonium salt which was prepared above under b. were dissolved in 15 ml of ethylene glycol dimethyl ether and the solution was cooled down to 0° C.; 280 mg (9.2 mmol) of sodium hydride were added and, after the mixture had been stirred at room temperature for 15 min, 1.56 g of the aldehyde described above under a., dissolved in 10 ml of ethylene glycol dimethyl ether, were subsequently added dropwise at 0° C.

After the mixture had been stirred at room temperature for 1.5 h and at 40° C. for a further 2 h, it was worked up using toluene and water and the insoluble material was removed by filtration. 2.6 g of oil were obtained from the toluene phase after drying and evaporating. Yield: crude product, 65% of theory.

The product was purified by chromatography (silica gel, methylene chloride/methanol).

$C_{29}H_{41}N_7$ (487).

1H NMR (CDCl$_3$): 1.3 (s,9H); 1.4 (s,9H); 2.6 (m,8H); 3.7 (m,7H); 6.2 (s,1H); 6.4 (d,1H); 7.0 (td,1H); 7.5 (m,3H); 7.7 (m,2H).

EXAMPLE 22

3-{4-[4-(2,6-Di-t-butylpyrimidin-4-yl)piperazin-1-yl]butyl}-4-methyl-5-phenyl-1,2,4-(4H)-triazole a. 2-[4-Methyl-5-phenyl-1,2,4-(4H)-triazol-3-yl]-1,3-dithiane 6.12 g (32.6 mmol) of the aldehyde prepared as described in Example 21 a. were dissolved in 16 ml of chloroform, after which 16 ml of acetic acid, 3.28 ml (32.6 mmol) of 1,3-dimercaptopropane and 160 µl of boron trifluoride etherate were added at 0° C. After the mixture had been refluxed for 2.5 h, a further 2.4 ml of dimercaptopropane and boron trifluoride etherate were slowly added and the mixture was heated for a further 6 h until the aldehyde had been completely reacted.

After the mixture had been cooled down to 0° C., it was adjusted to pH 9–10 with 10% strength sodium hydroxide solution, stirred at 0° C. for 1 h and then extracted 3 times with methylene chloride. 13.2 g of a yellow oil were obtained from the dried and evaporated solvent phase and were purified by column chromatography (silica gel, ethyl acetate). Yield: 4.3 g (48% of theory), colorless solid.

$C_{13}H_{15}N_3S_2$ (277).

1H NMR (CDCl$_3$): 2.1 (m,2H); 2.9 (m,2H); 3.3 (m,2H); 3.7 (s,3H); 5.3 (s,1H); 7.5 (m,3H); 7.7 (m,2H).

b. 831 mg (3 mmol) of the above-described dithiane were dissolved in 7.5 ml of dried THF, and the solution was treated, at −70° C., with 2.2 ml (3.6 mmol) of a 15% strength solution of butyllithium in n-hexane. After the mixture had been stirred at from −70° C. to −50° C. for 60 min, 1.06 g (3 mmol) of 1-chloro-3-[4-(2,6-di-t-butylpyrimidin-4-yl)piperazin-1-yl]propane (prepared by a method similar to Example 1, A.3), dissolved in 5 ml of THF, were added dropwise. The mixture was then warmed slowly to room temperature and heated at 30–50° C. for a further 60 min in order to achieve complete reaction. For the working-up, solid ammonium chloride was added to the cooled-down mixture and the latter was then added to ice/water; this mixture was then extracted several times with methylene chloride and methyl-t-butyl ether. Drying and concentrating left a residue of 1.74 g (98% of theory) of the substituted dithiane, which was subsequently hydrogenated in tetrahydrofuran, at 40° C. and over the course of 12 h, using Raney nickel and hydrogen. After the catalyst had been separated off, the residue was purified by chromatography (silica gel, methylene chloride/methanol). Yield: 700 mg (49% of theory). Colorless solid, m.p. 144–145° C.

$C_{29}H_{43}N_7$ (489).

EXAMPLE 23

3-{4-[4-(2-t-Butyl-6-trifluoromethylpyrimidin-4-yl)piperazin-1-yl]butyl}-4-methyl-5-phenyl-1,2,4-(4H)-triazole hydrochloride The compound was prepared, by a method similar to Example 22, using the chlorine compound from Example 1, A.3.

$C_{29}H_{34}F_3N_7$ (502)

1H NMR (CDCl$_3$): 1.3 (s,9H); 1.7 (m,2H); 1.9 (q,2H); 2.4 (t,2H); 2.5 (t,4H); 2.8 (t,2H); 3.6 (s,3H); 3.75 (m,4H); 6.6 (s,1H); 7.4 (m,3H); 7.6 (m,2H).

EXAMPLE 24

3-{3-[4-(2-t-Butyl-6-trifluoromethylpyrimidin-4-yl)piperazin-1-yl]propylmercapto}-5-(2,5-dimethylfuran-3-yl)-4-methyltriazole hydrochloride 2,5-Dimethylfuran-3-yl-3-mercapto-4-methyl-1,2,4-(4H)-triazole was obtained by reacting 2,5-dimethylfuran-3-carbonyl chloride with N-methylthiosemicarbazide and subsequently cyclizing in accordance with the method of Kubota and Uda, Chem. Pharm. Bull. (1975), 23, 955–966.

$C_9H_{11}N_3OS$ (209).

1H NMR (CDCl$_3$): 2.2 (s,3H); 2.3 (s,3H); 3.5 (s,3H); 6.5 (1H).

The abovementioned compound was obtained by reacting by a method similar to Example 1B. M.p. 190–192° C.

$C_{25}H_{34}F_3N_7OS$ HCl (574)

EXAMPLE 25

3-{3-[4-2-t-Butyl-6-trifluoromethylpyrimidin-4-yl)piperazin-1-yl]propylmercapto}-5-(pyrazin-2-yl)-4-methyltriazole hydrochloride 3-Mercapto-4-methyl-5-pyrazin-2-yl-1,2,4-(4H)-triazole was obtained by reacting pyrazine-2-carbonyl chloride by a method similar to the method of Kubota and Uda in Example 24.

The abovementioned compound was likewise prepared by a method similar to Example 1B. M.p. 164–169° C.

$C_{23}H_{31}F_3N_9$ (522).

EXAMPLE 65

3-(3-(4-(2-t-Butyl-6-trifluoromethyl-pyrimidin-4-yl)piperazin-1-yl)propylmercapto-4-methyl-5-((1H)-tetrazolyl-5)-1.2.4(4H)-triazole a) 3-(3-(4-(2-t-Butyl-6-trifluoromethylpyrimidine-4-yl)piperazin-1-yl)propylmercapto-4-methyl-1.2.4(4H)-triazole-5-carboxamide 950 mg (6.0 mmol) 5-mercapto-4-methyl-1.2.4(4H)-triazole-3-carboxamide were heated to 100° C. together with 2.2 g (6.0 mmol) of the chlorine base obtained according to example 1.A3 and 144 mg lithiumhydroxide (6.0 mmol) in 17 ml DMF for 3 h while stirring 100° C. The mixture was then cooled, 100 ml of water were added and the mixture was extracted with methyl-t-butyl ether. Then the solvent layer was dried and evaporated. The residue was purified by chromatography (silica gel, methylene chloride methanol 95:5).

Yield: 1.65 g (57% of th.)

mp: 141–143° C.

$C_{20}H_{29}F_3N_8OS$ (MG 486)

b) 3-(3-(4-(2-t-Butyl-6-trifluoromethylpyrrimidine-4-yl)piperazin-1-yl)propylmercapto-5-cyano-4-methyl-1.2.4(4H)-triazole 1.15 g (24.0 mmol) of the above described compound were dissolved in 20 ml of methylene chloride and 2 ml (12.0 mmol) of dipropylethylamine, cooled to 0° C. and 0.5 ml trifluoroacetanhydride were slowly added thereto. After stirring for 3 h at room temperature the mixture was washed twice with water, then with a 20% strength solution of NaHSO$_4$, with a saturated solution of NaHCO$_3$ and a saline solution; then the organic layer was dried and evaporated. The residue was 0.9 g of an oil (81% of th.). A sample was transferred into the hydrochloride with etherial hydrogen chloride.

mp: 220–222° C.

$C_{20}H_{27}F_3N_8S$ (MG 468)

$C_{20}H_{28}ClF_3N_8S$ (MG 503,5)

c) 5-(3-(4-(2-t-Butyl-6-trifluoromethylpyrimidine-4-yl)piperazin-1-yl)propylmercapto-4-methyl-3-((1H)-tetrazolyl-5)-1.2.4(4H)-triazole.

0.8 g (1.7 mmol) of the above described substance were dissolved in 1 ml of DMF, then 122 mg (1.9 mmol) of sodiumazide and 100 mg (1.9 mmol) of ammonium chloride were added and the mixture was heated to 85° C. for 2 h while stirring. For the working-up a little water was added, the solution was adjusted to pH 7 with NaOH and extracted with methylene chloride. Drying and concentrating left a residue of ca. 1 g which was purified by chromatography (silica gel, methylene chloride/methanol 8:2).

Yield: 0.38 g (43% of th.)

Fp. 133° (decomposition)

$C_{20}H_{28}F_3N_{11}S$ (MG 511)

The compounds listed in tables 2 to 9 were obtained in a similar way:

TABLE 2

Structure: Ar1-substituted triazole connected via A-linker to a ring containing X—Y, attached to a phenyl/pyridyl ring with T, Z, R7, R9, R10 substituents; R1 on triazole N.

| Ar1 | R1 | T | R7 | Z | R9 | R10 | X—Y | A |
|---|---|---|---|---|---|---|---|---|
| N—Me-2-Pyrrolyl | Et | N | tBut | N | 4-MeOPh | H | CH$_2$—N | COO—(CH$_2$)$_4$— |
| 2-Me-4-Oxazolyl | But | N | tBut | N | H | OMe | CH$_2$—N | S—CH$_2$—CH=CH—CH$_2$— |
| N—Me-2-Pyrrolyl | But | N | iProp | CH | tBut | H | CH$_2$—CH | S—(CH$_2$)$_3$— |
| 4-Imidazolyl | Me | N | tBut | CH | iProp | H | CH$_2$—N | S—(CH$_2$)$_7$— |
| 2,5-Di-methyl-furanyl-3- | cBut | N | Pyrrolyl | N | Me | H | CH=C | NH—(CH$_2$)$_4$ |
| N—Me-2-Pyrrolyl | Me | N | tBut | N | tBut | H | CH$_2$—CH | S—(CH$_2$)$_3$— |
| 2-Pyrrolyl | Me | N | 2,4 OMe—Ph | N | Cl | H | CH$_2$—N | O—(CH$_2$)$_3$— |
| 2-Pyrazinyl- | (CH$_2$)$_4$—OMe | N | tBut | N | 1-Pyrrolyl | H | CH$_2$—N | —(CH$_2$)$_8$— |
| 2-Methyl-pyridin-3-yl | CH$_2$Ph | CH | iProp | N | H | OMe | CH$_2$—N | —(CH$_2$)$_4$— |
| 2-Pyrazinyl- | cProp | CH | H | N | CH$_3$ | OMe | CH=C | O—(CH$_2$)$_3$— |
| 3-Br-Pyrimidin-5-yl | Et | N | Prop | N | cHex | H | CH=C | O—(CH$_2$)$_4$— |
| Pyrimidin-3-yl | Et | N | tBut | N | nHex | H | CH$_2$—N | S—CH$_2$—C(CH$_3$)=CH—CH$_2$— |
| N-Propyl-tetrazolyl | CH$_2$Ph | N | iProp | N | H | OMe | CH$_2$—N | S—(CH$_2$)$_4$— |
| 2-Methyl-pyridin-3-yl | cProp | N | H | N | CH$_3$ | OMe | CH=C | O—(CH$_2$)$_3$— |
| N-Ethyl-indol-3-yl | Me | N | H | N | iProp | OMe | CH$_2$—N | S—(CH$_2$)$_3$— |
| Tetrazolyl- | Et | N | tBut | N | H | CH$_3$ | CH$_2$—N | —(CH$_2$)$_4$— |
| 6-Chlor-biphenyl-2 | Me | CH | tBut | N | tBut | OMe | CH$_2$—N | CONH—(CH$_2$)$_4$— |
| 4-Methylthiazol | Me | N | 4-OMePh | N | Me | Me | CH$_2$—N | S—(CH$_2$)$_7$— |
| Tetrazonyl- | iProp | N | tBut | N | Ph | H | CH$_2$—N | CO—(CH$_2$)$_3$— |
| N—Me-2-Pyrrolyl | Prop | N | Me | CH | Pyrrolyl | H | CH=C | CH$_2$—CH$_2$—C(CH$_3$)=CH—CH$_2$— |
| 4-Imidazolyl | cProp | N | nPropyl | N | tBut | H | CH=C | NH—(CH$_2$)$_3$— |
| 2-Pyrrolyl | Me | N | 4-OMePh | N | Me | Me | CH=C | S—(CH$_2$)$_8$— |
| 3-Thienyl | Me | CH | 4-OMePh | N | Me | Me | CH$_2$—N | CH$_2$—CH$_2$—C(=CH$_2$)—CH$_2$— |
| 2-Me-4-Oxazolyl | Et | N | tBut | N | Pyrrolyl | H | CH$_2$—N | S—CH$_2$—C(=CH$_2$)—CH$_2$— |
| 2-Me-4-Oxazolyl | cProp | N | tBut | CH | Me | H | CH$_2$—N | S—CH$_2$—CH=CH—CH$_2$— |
| N-Propyl-tetrazolyl | Me | N | CF$_3$ | CH | Me | Butyl | CH=C | CH$_2$—CH$_2$—CH(CH$_3$)—CH$_2$ |
| 3-Thienyl | cProp | N | CF$_3$ | N | Me | Butyl | CH=C | CH$_2$—CH$_2$—CH(CH$_3$)—CH$_2$ |
| N-Propyl-tetrazolyl | Me | N | CF$_3$ | N | H | H | CH$_2$—N | —(CH$_2$)$_4$— |
| 3-Thienyl | cBut | N | CHF$_2$ | CH | H | H | CH$_2$—N | —(CH$_2$)$_4$— |
| 2,5-Dimethyl-furanyl-3- | Me | N | Pyrrolyl | CH | Me | H | CH=C | NH—(CH$_2$)$_4$— |
| Oxadiazol-2-yl | Prop | N | Me | N | Pyrrolyl | H | CH$_2$—N | —(CH$_2$)$_4$— |
| N-Propyl-2-pyrrolyl | Prop | N | Me | N | Pyrrolyl | H | CH=C | CH$_2$—CH$_2$—C(CH$_3$)=CH—CH$_2$— |
| 3-Benzthienyl | iProp | N | tBut | N | Ph | H | CH$_2$—N | CH$_2$—CH$_2$—CH(CH$_3$)—CH$_2$— |
| 5-Methyl imidazol-4-yl | Me | N | 2,4 OMe-Ph | CH | Cl | H | CH$_2$—N | O—(CH$_2$)$_3$— |
| 2-Aminothiazol-4yl | Prop | N | Cl | CH | iProp | H | CH$_2$—N | CH$_2$—CH$_2$—C(CH$_3$)=CH—CH$_2$— |
| N—Me-2-Pyrrolyl | iProp | CH | tBut | N | tBut | H | CH$_2$—CH | S—(CH$_2$)$_3$— |
| N-Propyl-2-pyrrolyl | Prop | N | Me | CH | tBut | H | CH=C | CH$_2$—CH$_2$—CH(CH$_3$)—CH$_2$— |
| 3-Benzthienyl | iProp | N | tBut | CH | H | Ne | CH$_2$—N | S—CH$_2$—C(CH$_3$)=CH—CH$_2$— |
| 2-Pyrrolyl | Me | CH | iProp | N | Me | H | CH$_2$—CH | NH—(CH$_2$)$_3$— |
| 2-Phenyl-furan-3yl | cProp | N | CF$_3$ | CH | CH | CH | CH=C | S—(CH$_2$)$_3$ |
| 3-Br-Pyrimidin-5-yl | Me | N | iProp | CH | tBut | H | CH$_2$—N | CO—(CH$_2$)$_7$— |
| 2-Aminothiazol-4yl | Et | N | CH | Cl | CH | CH | CH$_2$—N | CONH—(CH$_2$)$_4$— |
| 6 Me-Benzoindol-3-yl | Me | N | iProp | CH | Furanyl | H | CH$_2$—N | CH$_2$—CH$_2$—C(CH$_3$)=CH—CH$_2$— |
| 2,5-Dimethyl-furanyl-3- | cBut | CH | Pyrrolyl | N | Me | H | CH=C | NH—(CH$_2$)$_4$— |
| Tetrazolyl- | iProp | N | tBut | N | H | Cl | CH$_2$—N | CO—(CH$_2$)$_8$— |
| 4-Imidazolyl | (CH$_2$)$_4$—OMe | CH | tBut | N | H | H | CH$_2$—N | —(CH$_2$)$_8$— |
| Pyrimidin-3-yl | Et | CH | Pyrrolyl | N | cHex | H | CH=C | S—(CH$_2$)$_4$— |
| 4-Imidazolyl | Me | N | iProp | N | iProp | H | CH$_2$—N | S—(CH$_2$)$_7$— |
| N-Propyl-tetrazolyl | Et | CH | tBut | N | nHex | H | CH$_2$—N | S—CH$_2$—C(CH$_3$)=CH—CH$_2$— |

TABLE 3

| R1 | R2 | R3 | R4 | R5 | T | R7 | Z | R9 | R10 | X—Y | A |
|---|---|---|---|---|---|---|---|---|---|---|---|
| Me | H | CN | H | CN | N | tBut | N | tBut | H | CH$_2$—CH | S—(CH$_2$)$_3$— |
| Me | OMe | H | OMe | H | N | iProp | N | iProp | H | CH$_2$—N | S—(CH$_2$)$_7$— |
| Me | H | H | MeSO$_2$ | H | N | H | N | CF$_2$Cl | H | CH$_2$—N | O—(CH$_2$)$_3$— |
| Me | H | Me | CN | H | CH | tBut | N | tBut | H | CH$_2$—N | CONH—(CH$_2$)$_4$— |
| cProp | H | Me | CN | H | N | nPropyl | N | tBut | H | CH=C | NH—(CH$_2$)$_3$— |
| Me | OMe | H | tBut | H | N | 4-OMePh | N | Me | Me | CH=C | S—(CH$_2$)$_8$— |
| Me | H | iProp | H | Me | CH | 4-OMePh | N | Me | Me | CH$_2$—N | S—(CH$_2$)$_7$— |
| Et | H | H | H | H | N | Me | N | Pyrrolyl | H | CH$_2$—N | —(CH$_2$)$_4$— |
| iProp | H | H | H | H | N | Pyrrolyl | N | Me | H | CH$_2$—N | CO—(CH$_2$)$_8$— |
| Et | Me | H | Br | Br | CH | tBut | N | Pyrrolyl | H | CH$_2$—N | S—CH$_2$—C(=CH$_2$)—CH$_2$— |
| Et | H | H | 4-MePh | H | N | tBut | N | 2-Napht | H | CH$_2$—N | COO—(CH$_2$)$_4$— |
| —(CH$_2$)$_4$—OMe | H | Cl | Cl | H | N | tBut | N | 1-Pyrrolyl | H | CH$_2$—N | —(CH$_2$)$_8$— |
| Prop | Me | H | Br | H | CH | Me | N | Pyrrolyl | H | CH$_2$—N | S—CH$_2$—C(=CH$_2$)—CH$_2$— |
| Et | H | MeSO$_2$ | Me | MeSO$_2$ | N | Prop | N | cHex | H | CH=C | O—(CH$_2$)$_4$— |
| Et | Me | H | Br | H | N | tBut | N | nHex | H | CH$_2$—N | S—CH$_2$—C(CH$_3$)—CH—CH$_2$— |
| But | H | OMe | H | OMe | N | tBut | N | H | OMe | CH$_2$—N | S—CH$_2$—CH=CH—CH$_2$— |
| CH$_2$Ph | I | OMe | H | H | N | iProp | N | H | OMe | CH$_2$—N | S—(CH$_2$)$_4$— |
| cProp | H | Me | CN | H | N | nPropyl | CH | tBut | Me | CH=C | S—(CH$_2$)$_7$— |
| cProp | F | H | F | H | N | H | N | CH$_3$ | OMe | CH=C | O—(CH$_2$)$_3$— |
| Me | H | iProp | H | H | N | 4-OMePh | N | Me | Me | CH$_2$—N | S—(CH$_2$)$_7$— |
| Me | OMe | H | tBut | H | N | 4-OMePh | N | Me | Me | CH$_2$—N | CH$_2$—CH$_2$—C(=CH$_2$)—CH$_2$— |
| iProp | H | CN | CN | H | N | tBut | CH | H | Me | CH=C | S—CH$_2$—CH(CH$_3$)—CH$_2$— |
| Et | Me | H | Br | H | N | tBut | N | Pyrrolyl | H | CH$_2$—N | S—CH$_2$—C(=CH$_2$)—CH$_2$— |
| Me | H | OMe | H | Prop | N | iProp | N | Furanyl | H | CH$_2$—N | CH$_2$—CH$_2$—C(CH$_3$)=CH—CH$_2$— |
| Me | H | CN | H | H | N | tBut | CH | tBut | H | CH$_2$—CH | S—(CH$_2$)$_3$— |
| Me | OMe | H | OMe | H | N | iProp | CH | iProp | H | CH$_2$—N | —(CH$_2$)$_4$— |
| Me | H | H | MeSO$_2$ | H | N | H | C—Me | CF$_3$ | H | CH$_2$—N | CONH—(CH$_2$)$_4$ |
| Me | H | iProp | H | H | N | Me | CH | Me | H | CH$_2$—N | S—(CH$_2$)$_7$— |
| Prop | SO$_2$Me | H | SO$_2$Me | H | N | 4-OMePh | CH | Pyrrolyl | H | CH=C | CH$_2$—CH$_2$—C(CH$_3$)=CH—CH$_2$— |
| Me | OMe | H | tBut | H | N | 4-OMePh | CH | Me | Me | CH$_2$—N | CH$_2$—CH$_2$—C(=CH$_2$)—CH$_2$— |
| Prop | SO$_2$Me | H | SO$_2$Me | H | N | Me | N | Pyrrolyl | H | CH=C | CH$_2$—CH$_2$—C(CH$_3$)=CH—CH$_2$— |
| iProp | OMe | Ph | H | H | N | tBut | N | Ph | H | CH$_2$—N | CH$_2$—CH$_2$—CH(CH$_3$)—CH$_2$— |
| H | H | Br | H | NH$_2$ | N | Cl | CH | tBut | H | CH$_2$—N | S—CH$_2$—C(=CH$_2$)—CH$_2$— |
| Prop | H | C≡CH | H | H | CH | tBut | N | H | CH$_3$ | CH$_2$—N | CH$_2$—CH$_2$—CH(CH$_3$)—CH$_2$— |
| cProp | SO$_2$Me | H | SO$_2$Me | H | CH | Me | N | Pyrrolyl | H | CH=C | CH$_2$—CH$_2$—C(CH$_3$)=CH—CH$_2$— |
| iProp | OMe | Ph | H | H | CH | tBut | N | 4-OMePh | H | CH$_2$—N | —(CH$_2$)$_4$— |
| Me | H | H | H | H | N | Me | N | Pyrrolyl | But | CH=C | —(CH$_2$)$_8$— |
| Prop | NO$_2$ | H | H | Me | N | Me | N | Pyrrolyl | H | CH$_2$—N | —(CH$_2$)$_4$— |
| iProp | H | iProp | H | Me | N | tBut | N | Ph | H | CH$_2$—N | CO—(CH$_2$)$_3$— |
| Me | OMe | H | tBut | H | CH | 4-OMePh | N | Me | Me | CH$_2$—CH | CH$_2$—CH$_2$—C(=CH$_2$)—CH$_2$— |

TABLE 4

| R1 | R2 | R3 | R4 | R5 | R6 | R7 | R8 | R9 | R10 | X—Y | A |
|---|---|---|---|---|---|---|---|---|---|---|---|
| Me | OMe | H | tBut | H | H | tBut | H | tBut | H | $CH_2$—N | S—$CH_2$—C(=$CH_2$)—$CH_2$— |
| cProp | H | H | $MeSO_2$ | H | H | tBut | F | Ph | H | $CH_2$—N | O—$(CH_2)_4$— |
| Me | H | H | iProp | H | H | tBut | H | 1-Pyrrolyl | H | $CH_2$—N | S—$CH_2$—C($CH_3$)=CH—$CH_2$— |
| Prop | $SO_2Me$ | H | $SO_2Me$ | H | H | nPropyl | H | tBut | H | CH=C | S—$CH_2$—CH=CH—$CH_2$— |
| Me | H | Me | CN | H | H | $CF_3$ | H | tBut | H | $CH_2$—N | S—$(CH_2)_4$— |
| Me | OMe | H | tBut | H | Me | Me | H | iProp | H | $CH_2$—N | S—$CH_2$—CH($CH_3$)—$CH_2$ |
| Me | H | H | Cl | Cl | H | iProp | H | p-OMe—Ph | H | $CH_2$—N | O—$(CH_2)_3$— |
| cProp | H | Me | CN | H | OMe | tBut | CN | $CF_3$ | H | CH=C | S—$(CH_2)_7$— |
| Et | Me | H | Br | Br | H | iProp | H | Me | Me | CH=C | $CH_2$—$CH_2$—C(=$CH_2$)—$CH_2$— |
| Et | H | H | 4-MePh | H | H | iProp | H | F | OMe | $CH_2$—N | S—$(CH_2)_7$— |
| —$(CH_2)_4$—OMe | H | Cl | Cl | H | H | $CHF_2$ | H | But | H | $CH_2$—N | S—$CH_2$—C(=$CH_2$)—$CH_2$— |
| Prop | $SO_2Me$ | H | $SO_2Me$ | H | H | Ph | C≡CH | tBut | H | $CH_2$—N | $CH_2$—$CH_2$—C($CH_3$)=CH—$CH_2$— |
| iProp | OMe | Ph | H | H | H | $CHF_2$ | H | H | H | CH=C | S—$(CH_2)_3$— |
| cProp | F | H | F | H | H | $CF_3$ | H | H | H | $CH_2$—CH | —$(CH_2)_4$— |

TABLE 5

| Ar1 | R1 | R6 | R7 | R8 | R9 | R10 | X—Y | A |
|---|---|---|---|---|---|---|---|---|
| 4-Imidazolyl- | Me | H | tBut | H | tBut | H | $CH_2$—N | S—$CH_2$—C(=$CH_2$)—$CH_2$— |
| 2-Pyrazinyl- | cProp | H | tBut | F | Ph | H | $CH_2$—N | O—$(CH_2)_4$— |
| 2-Me-4-Oxazolyl- | Me | H | tBut | H | i-Pyrrolyl | H | $CH_2$—N | S—$CH_2$—C($CH_3$)=CH—$CH_2$— |
| 2-Pyrrolyl | Prop | H | nPropyl | H | tBut | H | CH=C | S—$CH_2$—CH=CH—$CH_2$— |
| 3-Br-Pyrimidin-5-yl- | Me | H | $CF_3$ | H | tBut | H | $CH_2$—N | S—$(CH_2)_4$— |
| Pyrimidin-3-yl- | Me | Me | Me | H | iProp | H | $CH_2$—N | S—$CH_2$—CH($CH_3$)—$CH_2$ |
| 6-Chlor-biphenyl-2- | Me | H | iProp | H | p-OMe—Ph | H | $CH_2$—N | O—$(CH_2)_3$— |
| 2,5-Di-methyl-furanyl-3- | cProp | OMe | tBut | CN | $CF_3$ | H | CH=C | S—$(CH_2)_7$— |
| N-Propyl-tetrazolyl- | Et | H | iProp | H | Me | Me | CH=C | $CH_2$—$CH_2$—C(=$CH_2$)—$CH_2$— |
| N—Methyl-2-Pyrrolyl- | Et | H | iProp | H | F | OMe | $CH_2$—N | S—$(CH_2)_7$— |
| 3-Thienyl | —$(CH_2)_4$—OMe | H | $CHF_2$ | H | But | H | $CH_2$—N | S—$CH_2$—C(=$CH_2$)—$CH_2$— |
| 3-Benzthienyl- | Prop | H | Ph | C≡CH | tBut | H | $CH_2$—N | $CH_2$—$CH_2$—C($CH_3$)=$CH_2$— |
| 2-Me-4-Oxazolyl- | iProp | H | $CHF_2$ | H | H | H | CH=C | S—$(CH_2)_3$— |
| 4-Methylthiazol- | Et | H | $CHF_2$ | H | But | H | $CH_2$—N | $CH_2$—$CH_2$—C($CH_3$)=$CH_2$— |
| 3-Benzthienyl- | iProp | H | iProp | H | p-OMe—Ph | H | $CH_2$—N | NH—$(CH_2)_4$— |
| 5-Methyl imidazol-4-yl- | Me | But | Me | H | H | H | $CH_2$—N | O—$(CH_2)_3$— |
| 2-Aminothiazol-4yl- | Prop | H | H | C≡CH | But | H | $CH_2$—N | —$(CH_2)_4$— |
| N—Me-2-Pyrrolyl- | Me | H | $CF_3$ | H | tBut | H | CH=C | CO—$(CH_2)_3$— |
| 2-Me-4-Oxazolyl | iProp | H | tBut | F | Ph | H | CH=C | S—$(CH_2)_9$— |
| 2,5-Dimethyl-furanyl- | Me | Me | H | CN | H | H | $CH_2$—N | S—$CH_2$—CH=CH—$CH_2$ |
| N-Ethyl-indol-3-yl | —$(CH_2)_4$—OMe | H | $CHF_2$ | H | Ph | H | CH=C | S—$(CH_2)_3$— |
| 2,5-Di-methyl-furanyl-3- | iProp | H | iProp | H | 2,4-OMe-Ph | Me | $CH_2$—CH— | —COO—$(CH_2)_4$— |
| 2-Aminothiazol-4yl- | Me | H | iProp | H | 2,4-OMe-Ph | H | CH=C— | —S—$CH_2$—CH=CH—$CH_2$— |
| 3-Br-Pyrimidin-5-yl- | Me | H | Me | H | Et | Me | $CH_2$—N | S—$(CH_2)_3$— |
| 5-Ethyl imidazol-4-yl- | cProp | Prop | H | C=CH | But | H | $CH_2$—N | —$(CH_2)_4$— |
| n-Butyl-tetrazolyl- | But | H | Et | CN | OH | H | CH=C | —$(CH_2)_4$— |

TABLE 5-continued

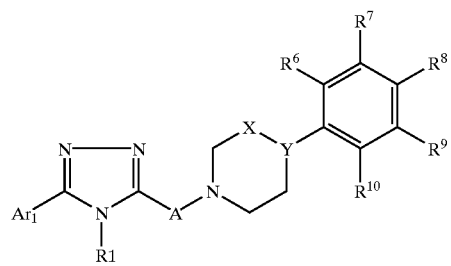

| Ar1 | R1 | R6 | R7 | R8 | R9 | R10 | X—Y | A |
|---|---|---|---|---|---|---|---|---|
| 3-Benzthienyl- | Me | H | CHF$_2$ | H | H | H | CH$_2$—CH- | S—(CH$_2$)$_3$— |
| N—Me-2-Pyrrolyl | Me | H | CF$_3$ | H | tBut | H | CH$_2$—CH- | S—(CH$_2$)$_3$ |
| Tetrazolyl- | cProp | H | CF$_3$ | H | iProp | H | CH$_2$—CH- | —(CH$_2$)$_4$— |
| Oxadiazol-2-yl- | cProp | H | CF$_3$ | H | H | H | CH═C | —(CH$_2$)$_4$— |

TABLE 6

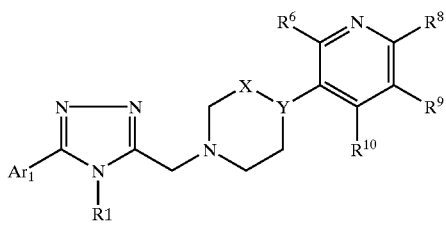

| Ar1 | R1 | R6 | R8 | R9 | R10 | X—Y | A |
|---|---|---|---|---|---|---|---|
| N—Me-2-Pyrrolyl | Prop | 4-MeOPh | H | tBut | H | CH$_2$—N | —S—(CH$_2$)$_7$— |
| 2-Me-4-Oxazolyl | Me | H | H | iProp | Me | CH$_2$—N | S—CH$_2$—CH═CH—CH$_2$— |
| 4-Imidazolyl | Me | iProp | Me | But | H | CH$_2$—N | COO—(CH$_2$)$_4$ |
| 2,5-Di-methyl-furanyl- | But | Me | CC | Me | H | CH═C | (CH$_2$)$_4$— |
| 3-Thienyl- | Me | H | H | Pyrrolyl | Cl | CH$_2$—CN | S—CH$_2$—C(CH$_3$)═CH—CH$_2$— |
| 2-Pyrazinyl- | cProp | H | CN | iProp | OMe | CH$_2$—N | —(CH$_2$)$_4$— |
| 3-Br-Pyrimidin-5-yl | Hex | H | H | iProp | OMe | CH$_2$—N | O—(CH$_2$)$_3$— |
| Pyrimidin-3-yl | Et | cHex | H | Prop | H | CH═C | NH—(CH$_2$)$_4$ |
| 2-Pyrazinyl- | Et | H | H | Pent | Et | CH$_2$—N | —(CH$_2$)$_4$— |
| 2-Methyl-pyridin-3-yl | Me | H | Cl | Me | H | CH$_2$—N | CONH—(CH$_2$)$_4$— |
| 2,5-Di-methyl-furanyl-3- | cProp | CH$_3$ | H | H | OMe | CH═C | —(CH$_2$)$_4$— |
| N-Ethyl-indol-3-yl- | cProp | CH$_3$ | Me | H | OMe | CH═C | S—CH$_2$—C(═CH$_2$)CH$_2$ |
| Tetrazolyl- | Et | cHex | H | Prop | H | CH═C | S—(CH$_2$)$_3$— |
| 3-Benzthienyl- | iPro | H | H | cProp | But | CH$_2$—N | S—(CH$_2$)$_8$— |
| N-Propyl-tetrazolyl | CH$_2$Ph | H | H | iProp | OMe | CH$_2$—N | S—(CH$_2$)$_4$— |
| 2-Aminothiazol-4yl- | Me | H | CN | CHF$_2$ | H | CH$_2$—N | —(CH$_2$)$_4$— |

TABLE 7

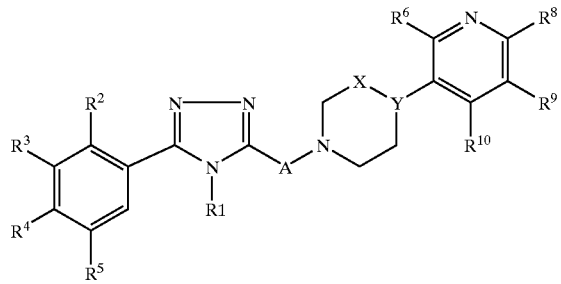

| R1 | R2 | R3 | R4 | R5 | R6 | R8 | R9 | R10 | X—Y | A |
|---|---|---|---|---|---|---|---|---|---|---|
| Prop | H | MeSO$_2$ | Me | MeSO$_2$ | Et | H | tBut | H | CH$_2$—N | COO—(CH$_2$)$_4$— |
| Me | Me | H | Br | H | H | H | H | H | CH$_2$—N | S—CH$_2$—CH═CH—CH$_2$— |
| Me | H | OMe | H | OMe | iProp | Me | tBut | H | CH$_2$—N | —(CH$_2$)$_4$— |

TABLE 7-continued

| R1 | R2 | R3 | R4 | R5 | R6 | R8 | R9 | R10 | X—Y | A |
|---|---|---|---|---|---|---|---|---|---|---|
| But | OMe | H | OMe | H | Me | C≡CH | Pyrrolyl- | H | CH=C | CONH—$(CH_2)_4$— |
| Me | H | Me | CN | H | H | H | Me | Cl | $CH_2$—N | —$(CH_2)_4$— |
| cProp | F | H | F | H | H | H | iProp | OMe | $CH_2$—N | S—$CH_2$—C(=$CH_2$)$CH_2$— |
| cProp | H | iProp | H | Me | $CH_3$ | Me | H | OMe | CH=C | O—$(CH_2)_3$— |
| Et | OMe | H | tBut | H | cHex | H | Prop | H | CH=C | S—$(CH_2)_3$— |
| Et | H | H | H | CN | nHex | CN | tBut | H | $CH_2$—N | S—$CH_2$—C($CH_3$)=CH—$CH_2$— |
| Hex | H | H | H | $H_2NSO_2$ | H | H | $CHF_2$ | H | $CH_2$—N | —CO—$(CH_2)_3$— |
| Me | H | H | H | H | H | H | iProp | H | CH=C | S—$(CH_2)_3$— |
| $CH_2$Ph | $NO_2$ | H | $NO_2$ | H | H | H | iProp | OMe | $CH_2$—N | S—$(CH_2)_4$— |

TABLE 8

| Ar1 | R1 | T | R7 | Z | R9 | R10 | X—Y—W | A |
|---|---|---|---|---|---|---|---|---|
| N—Me-2-Pyrrolyl- | Et | N | tBut | N | 4-MeOPh | H | $CH_2$—N—$CH_2$ | COO—$(CH_2)_4$— |
| 2-Me-4-Oxazolyl- | But | N | tBut | N | H | OMe | CH=C—$CH_2$ | S—$CH_2$—CH=CH—$CH_2$— |
| Oxadiazol-2-yl- | Prop | N | Me | N | Pyrrolyl | H | $CH_2$—CH—$CH_2$ | —$(CH_2)_4$— |
| Tetrazolyl- | iProp | N | tBut | N | Ph | H | $CH_2$—CH—$CH_2$ | CO—$(CH_2)_3$— |
| N—Me-2-Pyrrolyl- | Prop | N | Me | CH | Pyrrolyl | H | CH=C—$CH_2$ | $CH_2$—$CH_2$—C($CH_3$)=CH—$CH_2$— |
| 4-Imidazolyl- | cProp | N | nPropyl | N | tBut | H | $CH_2$—C=CH | NH—$(CH_2)_4$— |
| 2-Pyrrolyl | Me | N | 4-OMePh | N | Me | Me | $CH_2$—N—$CH_2$ | S—$(CH_2)_8$— |
| N—Me-2-Pyrrolyl | But | N | iProp | CH | tBut | H | $CH_2$—C=CH | S—$(CH_2)_3$— |
| N—Me-2-Pyrrolyl | Me | N | tBut | N | tBut | H | $CH_2$—N—$CH_2$ | S—$(CH_2)_3$— |
| 2-Pyrrolyl | Me | N | 2,4 OMe—Ph | N | Cl | H | $CH_2$—C=CH | CONH—$(CH_2)_4$— |
| 2-Pyrazinyl- | $(CH_2)_4$—OMe | N | tBut | N | 1-Pyrrolyl | H | $CH_2$—C=CH | O—$(CH_2)_3$— |
| 2-Methyl-pyridin-3-yl- | $CH_2$Ph | CH | iProp | N | H | OMe | $CH_2$—N—$CH_2$ | —$(CH_2)_4$— |
| 2-Pyrazinyl- | cProp | CH | H | N | $CH_3$ | OMe | $CH_2$—N—$CH_2$ | —$(CH_2)_8$— |
| 3-Br-Pyrimidin-5-yl- | Et | N | Prop | N | cHex | H | CH=C—$CH_2$ | —$(CH_2)_4$— |
| Pyrimidin-3-yl- | Et | N | tBut | N | nHex | H | $CH_2$—C=CH | S—$CH_2$—C($CH_3$)=CH—$CH_2$— |
| N-Propyl-tetrazolyl- | $CH_2$Ph | N | iProp | N | H | OMe | $CH_2$—N—$CH_2$ | S—$(CH_2)_4$— |
| 2-Methyl-pyridin-3-yl- | cProp | N | H | N | $CH_3$ | OMe | $CH_2$—N—$CH_2$ | O—$(CH_2)_3$— |
| 4-Imidazolyl- | Me | N | tBut | CH | iProp | H | $CH_2$—N—$CH_2$ | S—$(CH_2)_7$— |
| 2,5-Di-methyl-furanyl-3- | cBut | N | Pyrrolyl | N | Me | H | $CH_2$—N—$CH_2$ | NH—$(CH_2)_4$ |
| N-Ethyl-indol-3-yl- | Me | N | H | N | iProp | OMe | CH=C—$CH_2$ | S—$(CH_2)_3$— |
| Tetrazolyl- | Et | N | tBut | N | H | $CH_3$ | $CH_2$—C=CH | —$(CH_2)_4$— |
| 6-Chlor-biphenyl-2 | Me | CH | tBut | N | tBut | OMe | CH=C—$CH_2$ | CONH—$(CH_2)_4$ |
| 4-Methylthiazol- | Me | N | 4-OMePh | N | Me | Me | CH=C—$CH_2$ | S—$(CH_2)_7$— |
| 3-Thienyl- | cBut | N | $CHF_2$ | CH | H | H | $CH_2$—N—$CH_2$ | —$(CH_2)_4$ |
| 2,5-Di-methyl-furanyl-3- | Me | N | Pyrrolyl | CH | Me | H | $CH_2$—N—$CH_2$ | NH—$(CH_2)_4$ |
| 3-Thienyl | Me | CH | 4-OMePh | N | Me | Me | $CH_2$—$CH_2$—$CH_2$ | $CH_2$—$CH_2$—C(=$CH_2$)—$CH_2$— |
| 2-Me-4-Oxazolyl- | Et | N | tBut | N | Pyrrolyl | H | $CH_2$—C=CH | S—$CH_2$—C(=$CH_2$)—$CH_2$— |
| 2-Me-4-Oxazolyl- | cProp | N | tBut | CH | Me | H | $CH_2$—N—$CH_2$ | $CH_2$—$CH_2$—CH($CH_3$)—$CH_2$ |
| N-Propyl-tetrazolyl- | Me | N | $CF_3$ | CH | Me | Butyl | $CH_2$—N—$CH_2$ | $CH_2$—$CH_2$—CH($CH_3$)—$CH_2$ |
| 3-Thienyl- | cProp | N | $CF_3$ | N | Me | Butyl | $CH_2$—N—$CH_2$ | S—$CH_2$—CH=CH—$CH_2$— |
| N-Propyl-tetrazolyl- | Me | N | $CF_3$ | N | H | H | $CH_2$—CH—$CH_2$ | —$(CH_2)_4$ |
| N-Propyl-2-Pyrrolyl- | Prop | N | Me | N | Pyrrolyl | H | $CH_2$—N—$CH_2$ | $CH_2$—$CH_2$—C($CH_3$)=CH—$CH_2$— |
| 3-Benzthienyl- | iProp | N | tBut | N | Ph | H | $CH_2$—N—$CH_2$ | $CH_2$—$CH_2$—CH($CH_3$)—$CH_2$ |
| 5-Methyl imidazol-4-yl- | Me | N | 2,4 OMe-Ph | CH | Cl | H | CH=C—$CH_2$ | O—$(CH_2)_3$— |
| 2-Aminothiazol-4yl- | Prop | N | Cl | CH | iProp | H | CH=C—$CH_2$ | $CH_2$—$CH_2$—C($CH_3$)=CH—$CH_2$— |
| N—Me-2-Pyrrolyl | iProp | CH | tBut | N | tBut | H | $CH_2$—CH—$CH_2$ | S—$(CH_2)_3$— |

TABLE 8-continued

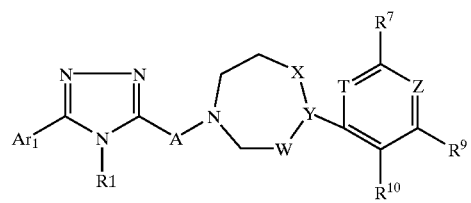

| Ar1 | R1 | T | R7 | Z | R9 | R10 | X—Y—W | A |
|---|---|---|---|---|---|---|---|---|
| N-Propyl-2-Pyrrolyl | Prop | N | Me | CH | tBut | H | CH=C—CH$_2$ | CH$_2$—CH$_2$—CH(CH$_3$)—CH$_2$ |
| 2-Pyrrolyl | Me | CH | iProp | N | Me | H | CH$_2$—N—CH$_2$ | N—(CH$_2$)$_3$— |
| 2-Phenyl-furan-3yl- | cProp | N | CF$_3$ | CH | CH | CH | CH$_2$—CH—CH$_2$ | S—(CH$_2$)$_3$ |
| 3-Br-Pyrimidin-5-yl- | Me | CH | iProp | N | tBut | H | CH=C—CH$_2$ | CO—(CH$_2$)$_7$— |
| 2-Aminothiazol-4yl- | Et | N | CH | Cl | CH | CH | CH$_2$—N—CH$_2$ | CONH—(CH$_2$)$_4$— |
| 6 Me-Benzoindol-3-yl | Me | N | iProp | CH | Furanyl | H | CH$_2$—N—CH$_2$ | CH$_2$—CH$_2$—C(CH$_3$)=CH—CH$_2$— |
| 2,5-Di-methyl-furanyl-3- | cBut | CH | Pyrrolyl | N | Me | H | CH$_2$—CH—CH$_2$ | NH—(CH$_2$)$_4$ |
| Tetrazolyl- | iProp | N | tBut | CH | H | Cl | CH$_2$—N—CH$_2$ | CO—(CH$_2$)$_8$ |
| 4-Imidazolyl- | (CH$_2$)$_4$—OMe | CH | tBut | N | H | H | CH$_2$—N—CH$_2$ | —(CH$_2$)$_8$— |
| Pyrimidin-3-yl- | Et | CH | Pyrrolyl | N | cHex | H | CH=C—CH$_2$ | S—(CH$_2$)$_4$— |
| 4-Imidazolyl- | Me | N | iProp | N | iProp | H | CH$_2$—CH—CH$_2$ | S—(CH$_2$)$_7$— |
| N-Propyl-tetrazolyl- | Et | CH | tBut | N | nHex | H | CH$_2$—N—CH$_2$ | S—CH$_2$—C(CH$_3$)=CH—CH$_2$— |

TABLE 9

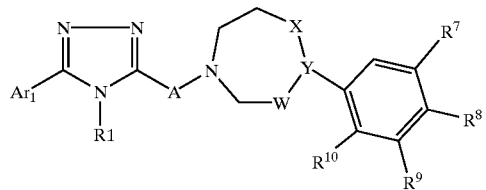

| Ar1 | R1 | R6 | R7 | R8 | R9 | R10 | X—Y—W | A |
|---|---|---|---|---|---|---|---|---|
| 2-Pyrrolyl | Prop | H | nPropyl | H | tBut | H | CH$_2$—CH—CH$_2$ | S—CH$_2$—CH=CH—CH$_2$— |
| N-Ethyl-indol-3-yl | —(CH$_2$)$_4$—OMe | H | CHF$_2$ | H | H | H | CH$_2$—C=CH | S—(CH$_2$)$_3$— |
| 2,5-Di-methyl-furanyl-3- | iProp | H | iProp | H | 2,4-OMe—Ph | Me | CH=C—CH$_2$ | —COO—(CH$_2$)$_4$— |
| 3-Br-Pyrimidin-5-yl- | Me | Me | Me | H | iProp | H | CH$_2$—C=CH | S—CH$_2$—CH(CH$_3$)—CH$_2$ |
| Pyrimidin-3-yl- | Hexyl | H | CF$_3$ | H | tBut | H | CH=C—CH$_2$ | S—(CH$_2$)$_4$— |
| 6-Chlor-biphenyl-2- | Me | H | iProp | H | p-OMe—Ph | H | CH$_2$—N—CH$_2$ | O—(CH$_2$)$_3$— |
| N-Propyl-tetrazolyl- | Et | H | iProp | H | Me | Me | CH$_2$—N—CH$_2$ | CH$_2$—CH$_2$—C(=CH$_2$)—CH$_2$— |
| N—Methyl-2-Pyrrolyl- | Et | H | iProp | H | F | OMe | CH$_2$—C=CH | S—(CH$_2$)$_7$— |
| 3-Thienyl | —(CH$_2$)$_4$—OMe | H | CHF$_2$ | H | But | H | CH$_2$—C=CH | S—CH$_2$—C(=CH$_2$)—CH$_2$— |
| 2,5-Di-methyl-furanyl-3- | cProp | OMe | tBut | CN | CF$_3$ | H | CH$_2$—C=CH | CO—(CH$_2$)$_3$— |
| 2-Aminothiazol-4yl- | Me | H | iProp | H | 2,4-OMe—Ph | H | CH=C—CH$_2$ | —S—CH$_2$—CH=CH—CH$_2$— |
| 3-Benzthienyl- | Pentyl | H | Ph | C≡CH | tBut | H | CH$_2$—N—CH$_2$ | CH$_2$—CH$_2$—C(CH$_3$)=CH—CH$_2$— |
| 4-Methylthiazol- | Et | H | CHF$_2$ | H | But | H | CH=C—CH$_2$ | CH$_2$—CH$_2$—C(CH$_3$)=CH—CH$_2$— |
| 3-Benzthienyl- | iProp | H | iProp | H | p-OMe—Ph | H | CH$_2$—C=CH | —CONH—(CH$_2$)$_4$ |
| 5-Methyl imidazol-4-yl- | Me | But | Me | H | H | H | CH$_2$—N—CH$_2$ | O—(CH$_2$)$_3$— |
| 2-Aminothiazol-4yl- | Prop | H | H | C≡CH | But | H | CH$_2$—N—CH$_2$ | —(CH$_2$)$_4$— |
| 2-Me-4-Oxazolyl- | iProp | H | CHF$_2$ | H | H | H | CH$_2$—N—CH$_2$ | —(CH$_2$)$_4$— |
| N—Me-2-Pyrrolyl | Me | H | CF$_3$ | H | tBut | H | CH$_2$—C=CH | S—(CH$_2$)$_7$— |
| 2-Me-4-Oxazolyl | iProp | H | tBut | F | Ph | H | CH$_2$—N—CH$_2$ | CONH(CH$_2$)$_4$— |
| 2,5-Dimethyl-furanyl- | Me | Me | H | CN | H | H | CH=C—CH$_2$ | S—CH$_2$—CH=CH—CH$_2$ |
| 3-Br-Pyrimidin-5-yl- | Me | H | Me | H | Et | Me | CH$_2$—N—CH$_2$ | S—(CH$_2$)$_3$— |
| n-Butyl-tetrazolyl- | But | H | Et | CN | OH | H | CH$_2$—N—CH$_2$ | —(CH$_2$)$_4$— |
| 3-Benzthienyl- | Me | H | CHF$_2$ | H | H | H | CH$_2$—C=CH | S—(CH$_2$)$_3$— |
| N—Me-2-Pyrrolyl | Me | H | CF$_3$ | H | tBut | H | CH$_2$—C—CH$_2$ | S—(CH$_2$)$_3$ |
| Tetrazolyl- | cProp | H | iProp | H | CF$_3$ | H | CH$_2$—N—CH$_2$ | —(CH$_2$)$_4$— |
| Propyl-tetrazolyl- | Et | H | CF$_3$ | H | nProp | H | CH$_2$—N—CH$_2$ | —(CH$_{13}$)$_4$— |
| Oxadiazol-2-yl- | cProp | H | CF$_3$ | H | H | H | CH$_2$—N—CH$_2$ | —(CH$_2$)$_4$— |
| 5-Ethyl imidazol-4-yl- | cProp | Prop | H | C≡CH | But | H | CH$_2$—N—CH$_2$ | —(CH$_2$)$_4$— |
| 4-Imidazolyl- | Me | H | tBut | H | tBut | H | CH$_2$—N—CH$_2$ | S—CH$_2$—C(=CH$_2$)—CH$_2$— |
| 2-Pyrazinyl- | cProp | H | tBut | F | Ph | H | CH=C—CH$_2$ | O—(CH$_2$)$_4$— |
| 2-Me-4-Oxazolyl- | Me | H | tBut | H | 1-Pyrrolyl | H | CH$_2$—CH—CH$_2$ | S—CH$_2$—C(CH$_3$)=CH—CH$_2$— |
| 4-Pyrimidyl- | Et | H | Pent | H | 2,4-OMe—Ph | H | CH$_2$—N—CH$_2$ | |
| Oxadiazol-2-yl- | Hex | H | CF$_3$ | H | tBut | H | CH$_2$—N—CH$_2$ | S—(CH$_2$)$_4$— |

Examples of Pharmacological Administration Forms

Tablets of the following composition were molded, in a customary manner, on a compressed-tablet machine:

A) Tablets

| | |
|---|---|
| 40 mg | of the substance of Example 1 |
| 120 mg | of corn starch |
| 13.5 mg | of gelatin |
| 45 mg | of lactose |
| 2.25 mg | of Aerosil ® (chemically pure silicic acid which is finely divided to the submicroscopic level) |
| 6.75 mg | of potato starch (as a 6% strength paste) |

B) Coated tablets

| | |
|---|---|
| 20 mg | of the substance of Example 4 |
| 60 mg | of core mass |
| 70 mg | of saccharifying mass |

The core mass consists of 9 parts of corn starch, 3 parts of lactose and 1 part of vinylpyrrolidone/vinyl acetate 60:40 mixed polymer. The saccharifying mass consists of 5 parts of cane sugar, 2 parts of corn starch, 2 parts of calcium carbonate and 1 part of talc. The coated tablets which have been prepared in this way are then provided with a gastric juice-resistant coating.

Biological Investigations—Receptor-binding Studies

1) $D_3$-binding Test

Cloned human $D_3$ receptor-expressing CCL 1,3 mouse fibro-blasts, which can be obtained from Res. Biochemicals Internat., One Strathmore Rd., Natick, Mass. 01760-2418 USA, were used for the binding studies.

Cell Preparation

The $D_3$-expessing cells were multiplied in RPMI-1640 containing 10% fetal calf serum (GIBCO No. 041-32400 N); 100 U/ml penicillin and 0.2% streptomycin (GIBCO BRL, Gaithersburg, Md., USA). After 48 h, the cells were washed with PBS and incubated for 5 min with 0.05% trypsin-containing PBS. After that, the mixture was neutralized with medium and the cells were collected by centrifuging at 300 g. In order to lyse the cells, the pellet was briefly washed with lysis buffer (5mM tris-HCl, pH 7.4, containing 10% glycerol) and then incubated, at 4° C. for 30 min, at a concentration of 107 cells/ml of lysis buffer. The cells were centrifuged at 200 g for 10 min and the pellet was stored in liquid nitrogen.

Binding Tests

For the $D_3$ receptor-binding test, the membranes were suspended in incubation buffer (50 mM tris-HCl, pH 7.4, containing 120 mM NaCl, 5 mM KCl, 2 mM $CaCl_2$, 2 mM $MgCl_2$, 10 $\mu$M quinolinol, 0.1% of ascorbic acid and 0.1% BSA) at a concentration of approx. $10^6$ cells/250 $\mu$l of test mixture and incubated at 30° C. with 0.1 nM $^{125}$iodosulpride in the presence and absence of test substance. The nonspecific binding was determined using $10^{-6}$M spiperone.

After 60 min, the free and the bound radio ligand were separated by filtration through GF/B glass fiber filters (Whatman, England) on a Skatron cell collector (Skatron, Lier, Norway) and the filters were washed with ice-cold tris-HCl buffer, pH 7.4. The radioactivity which had collected on the filters was quantified using a Packard 2200 CA liquid scintillation counter.

The $K_i$ values were determined by means of nonlinear regression analysis using the LIGAND program.

2) $D_2$-binding Test

Cell Culture

HEK-293 cells, possessing stably expressed human dopamine D2A receptors, were cultured in RPMI 1640 containing Glutamax I™ and 25 mM HEPES containing 10% fetal calf serum albumin. All the media contained 100 units of pencillin per ml and 100 $\mu$g/ml streptomycin. The cells were kept at 37° C. in a moist atmosphere containing 5% $Co_2$.

The cells were prepared for the binding studies by being trypsinized (0.05% trypsin solution) at room temperature for 3–5 minutes. After that, the cells were centrifuged at 250 g for 10 minutes and treated, at 4° C. for 30 minutes, with lysis buffer (5 mM tris-HCl, 10% glycerol, pH 7.4). Following centrifugation at 250 g for 10 minutes, the residue was stored at −20° C. until used.

Receptor Binding Tests

Dopamine $D_2$ receptor "low affinity state" using $^{125}$I-spiperone (81 TBq/mmol, Du Pont de Nemours, Dreieich)

The mixtures (1 ml) were composed of $1\times10^5$ cells in incubation buffer (50 mM tris, 120 mM NaCl, 5 mM KCl, 2 mM $MgCl_2$ and 2 mM $CaCl_2$, pH 7.4 with HCl) and 0.1 nM $^{125}$I-spiperone (total binding) or, in addition, 1 $\mu$M haloperidol (nonspecific binding) or test substance.

After having been incubated at 25° C. for 60 minutes, the mixtures were filtered through GF/B glass fiber filters (Whatman, England) on a Skatron cell collector (Zinsser, Frankfurt) and the filters were washed with ice-cold 50 mM tris-HCl buffer, pH 7.4. The radioactivity which had collected on the filters was quantified using a Packard 2200 CA liquid scintillation counter.

The evaluation was carried out as described under a).

The $K_i$ values were determined by means of nonlinear regression analysis using the LIGAND program or by converting the $IC_{50}$ values with the aid of the formula of Cheng and Prusoff.

In these tests, the novel compounds exhibit very good affinities for the $D_3$ receptor (<1 $\mu$molar, in particular <100 nmolar) and high selectivities in relation to the $D_3$ receptor.

We claim:

1. A triazole compound of formula I

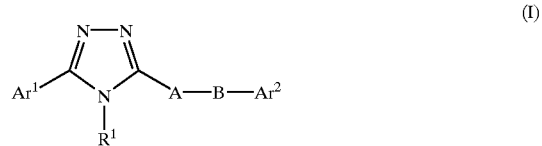

where
Ar$^1$ is phenyl, naphthyl or a 5- or 6-membered heterocyclic aromatic ring having from 1 to 4 heteroatoms which are independently selected from O, S and N, where Ar$^1$ is unsubstituted or substituted by 1, 2, 3 or 4 substituents selected from
$C_1$–$C_6$-alkyl which is unsubstituted or substituted by OH, $OC_1$–$C_6$-alkyl, halogen or phenyl,
$C_1$–$C_6$-alkoxy, $C_2$–$C_6$-alkenyl, $C_2$–$C_6$-alkynyl, $C_3$–$C_6$-cycloalkyl, halogen, CN, $COOR^2$, $NR^2R^2$, $NO_2$, $SO_2R^2$, $SO_2NR^2R^2$, OH, and
phenyl which is unsubstituted or substituted by $C_1$–$C_6$-alkyl, $OC_1$–$C_6$-alkyl, $NR^2R^2$, CN, $CF_3$, $CHF_2$, or halogen, and where the 5- or 6-membered heterocyclic ring may be fused to a phenyl ring;
A is a straight-chain or branched $C_4$–$C_{10}$-alkylene group or a straight-chain or branched group consisting of from 4 to 11 members selected from the group of from 3 to 10 methylene members and at least one member Z, wherein Z is selected from O, S, NR², CONR², COO, CO, a double bond and a triple bond, and the member(s) Z is(are) arranged within the chain linking the triazole ring to B between methylene members and/or between the triazole ring and a methylene member;

B is a radical of the formula:

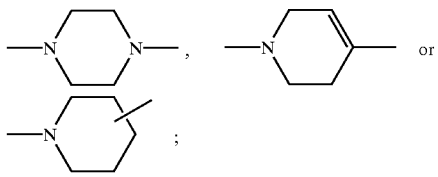

Ar² is phenyl, pyridyl, pyrimidinyl or triazinyl, where Ar² is unsubstituted or substituted by from 1 to 4 substituents selected from OR², $C_1$–$C_6$-alkyl, $C_2$–$C_6$-alkenyl, $C_2$–$C_6$-alkynyl, $C_1$–$C_6$-alkoxy-$C_1$–$C_6$-alkyl, halogen-$C_1$–$C_6$-alkyl, halogen-$C_1$–$C_6$-alkoxy, halogen, CN, NO₂, SO₂R², NR²R², SO₂NR²R², a 5- or 6-membered carbocyclic, aromatic or non-aromatic ring and a 5- or 6-membered, heterocyclic aromatic or non-aromatic ring having from 1 or 2 heteroatoms which are selected from O, S and N, where the carbocyclic or heterocyclic ring is unsubstituted or substituted by $C_1$–$C_6$-alkyl, phenyl, phenoxy, halogen, OC₁–C₆-alkyl, OH, NO₂ or CF₃ and/or is optionally fused to a phenyl ring;

and where Ar² may be fused to a carbocyclic aromatic or non-aromatic ring or 5- or 6-membered heterocyclic aromatic or non-aromatic ring having 1 or 2 heteroatoms, selected from O, S and N, R¹ is $C_3$–$C_6$-cycloalkyl or $C_1$–$C_6$-alkyl which is unsubstituted or substituted by OH or OC₁–C₆-alkyl;

the radicals R², which can be identical or different, are H or $C_1$–$C_6$-alkyl which is unsubstituted or substituted by OH, OC₁–C₆-alkyl or phenyl;

or a salt thereof with a physiologically tolerated acid.

2. The compound of formula I defined in claim 1, where A is a $C_4$–$C_{10}$-alkylene group or a group consisting of from 4 to 11 members selected from the group of from 3 to 10 methylene members and at least one group Z, wherein Z is selected from O, S, a double bond and triple bond.

3. The compound of formula I defined in claim 1, where Ar¹ is phenyl, naphthyl, pyrrolyl, thienyl, furanyl, thiazolyl, imidazolyl, oxazolyl, oxadiazolyl, tetrazolyl, isoxazolyl, pyridinyl, pyrazinyl, pyrimidinyl, benzthiophenyl, indolyl or benzofuranyl, where Ar¹ is optionally substituted or fused as indicated in claim 1.

4. The compound of formula I defined in claim 3, where Ar¹ is phenyl, thienyl, furanyl, tetrazolyl, pyrrolyl or pyrazinyl, where Ar¹ is optionally substituted as indicated in claim 3.

5. The compound of formula I defined in claim 1, where Ar¹ is unsubstituted or substituted by 1, 2, 3 or 4 substituents selected from CN, $C_1$–$C_6$-alkyl, OH, OC₁–C₆-alkyl, phenyl and halogen.

6. The compound of formula I defined in claim 1, where R¹ is $C_1$–$C_6$-alkyl or $C_3$–$C_6$-cycloalkyl.

7. The compound of formula I defined in claim 1, where Ar² is phenyl, pyridinyl or pyrimidinyl and wherein Ar² is unsubstituted or carries one or two substituents selected from $C_1$–$C_6$-alkyl, $C_2$–$C_6$-alkynyl, halogen, CN, halogen-$C_1$–$C_6$-alkyl, OC₁–C₆-alkyl, NO₂, phenyl pyrrolyl, imidazolyl, pyrazolyl thienyl, indolyl, cyclopentyl and cyclohexyl.

8. The compound of formula I defined in claim 7, wherein the substituent(s) is/are selected from $C_1$–$C_6$-alkyl, phenyl, NO₂, and halogen-$C_1$–$C_6$-alkyl.

9. The compound of formula I defined in claim 7, wherein the substituent(s) is/are selected from CF₃, CHF₂ and CF₂Cl.

10. A compound of formula I

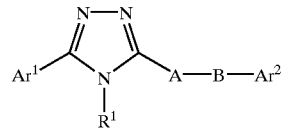

where

Ar¹ is phenyl which is unsubstituted or substituted by $C_1$–$C_6$-alkyl, OC₁–C₆-alkyl, CN, phenyl or halogen;

A is a straight-chain or branched $C_4$–$C_{10}$-alkylene group or a straight-chain or branched group consisting of from 4 to 11 members selected from the group of from 3 to 10 methylene members and at least one member Z, wherein Z is selected from O, S, NR², CONR², COO, CO, a double bond and a triple bond, is

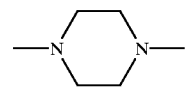

10 and

Ar² is pyrimidinyl which is unsubstituted or substituted by $C_1$–$C_6$-alkyl, halogen-$C_1$–$C_6$-alkyl, halogen-$C_1$–$C_6$-alkoxy, pyrrolyl or indolyl;

R¹ is $C_3$–$C_6$-cycloalkyl or $C_1$–$C_6$-alkyl which is unsubstituted or substituted by OH or OC₁–C₆-alkyl;

the radicals R², which can be identical or different, are H or $C_1$–$C_6$-alkyl which is unsubstituted or substituted by OH, OC₁–C₆-alkyl or phenyl;

or a salt thereof with a physiologically tolerated acid.

11. The compound of formula I defined in claim 10, where Ar¹ is phenyl which is unsubstituted or substituted by $C_1$–$C_6$-alkyl, OC₁–C₆-alkyl or halogen, and A is —S(CH₂)$_{3-10}$— or —(CH₂)$_{4-10}$—.

12. A pharmaceutical composition comprising an effective amount of at least one compound of formula I as defined in claim 1, and a physiologically acceptable carrier substance and/or auxiliary substance.

13. A method for the treatment of a disease which responds to dopamine D3 receptor antagonists or dopamine D3 agonists and which is selected from the group of schizophrenia, depressions, neuroses, psychoses, Parkinson's disease and anxiety, which method comprises administering an effective amount of at least one compound of formula I

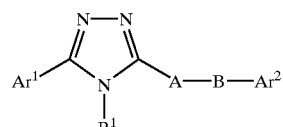

where

Ar¹ is phenyl, naphthyl or a 5- or 6-membered heterocyclic aromatic ring having from 1 to 4 heteroatoms which are independently selected from O, S and N, where $Ar^1$ is unsubstituted or substituted by 1, 2, 3 or 4 substituents selected from $C_1$–$C_6$-alkyl which is unsubstituted or substituted by OH, $OC_1$–$C_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, $COOR^2$, $NR^2R^2$, $NO_2$, $SO_2R^2$, $SO_2NR^2R^2$, OH, and phenyl which is unsubstituted or substituted by $C_1$–$C_6$-alkyl, $OC_1$–$C_6$-alkyl, $NR^2R^2$, CN, $CF_3$, $CHF_2$, or halogen, and where the 5- or 6-membered heterocyclic ring may be fused to a phenyl ring;

A is a straight-chain or branched $C_4$–$C_{10}$-alkylene group or a straight-chain or branched group consisting of from 4 to 11 members selected from the group of from 3 to 10 methylene members and at least one member Z, wherein Z is selected from O, S, $NR^2$, $CONR^2$, COO, CO, a double bond and a triple bond, B is a radical of the formula:

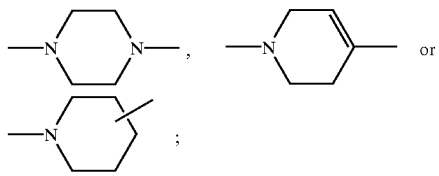

$Ar^2$ is phenyl, pyridyl, pyrimidinyl or triazinyl, where $Ar^2$ is unsubstituted or substituted by from 1 to 4 substituents selected from $OR^2$, $C_1$–$C_6$-alkyl, $C_2$–$C_6$-alkenyl, $C_2$–$C_6$-alkynyl, $C_1$–$C_6$-alkoxy-$C_1$–$C_6$-alkyl, halogen-$C_1$–$C_6$-alkyl, halogen-$C_1$–$C_6$-alkoxy, halogen, CN, $NO_2$, $SO_2R^2$, $NR^2R^2$, $SO_2NR^2R^2$, a 5- or 6-membered carbocyclic, aromatic or non-aromatic ring and a 5- or 6-membered, heterocyclic aromatic or non-aromatic ring having from 1 or 2 heteroatoms which are selected from O, S and N, where the carbocyclic or heterocyclic ring is unsubstituted or substituted by $C_1$–$C_6$-alkyl, phenyl, phenoxy, halogen, $OC_1$–$C_6$-alkyl, OH, $NO_2$ or $CF_3$ and/or is optionally fused to a phenyl ring;

and where $Ar^2$ may be fused to a carbocyclic aromatic or non-aromatic ring or 5- or 6-membered heterocyclic aromatic or non-aromatic ring having 1 or 2 heteroatoms, selected from O, S and N, $R^1$ is $C_3$–$C_6$-cycloalkyl or $C_1$–$C_6$-alkyl which is unsubstituted or substituted by OH, $OC_1$–$C_6$-alkyl or phenyl;

the radicals $R^2$, which can be identical or different, are H or $C_1$–$C_6$-alkyl which is unsubstituted or substituted by OH, $OC_1$–$C_6$-alkyl or phenyl;

or a salt thereof with a physiologically tolerated acid, to a subject in need of such treatment.

14. A compound of formula VIII

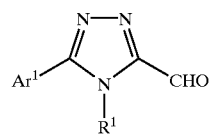

(VIII)

where $Ar^1$ is phenyl, naphthyl or a 5- or 6-membered heterocyclic aromatic ring having from 1 to 4 heteroatoms which are independently selected from O, S and N, where $Ar^1$ is unsubstituted or substituted by 1, 2, 3 or 4 substituents selected from $C_1$–$C_6$-alkyl which is unsubstituted or substituted by OH, $OC_1$–$C_6$-alkyl, halogen or phenyl, $C_1$–$C_6$-alkoxy, $C_2$–$C_6$-alkenyl, $C_2$–$C_6$-alkynyl, $C_3$–$C_6$-cycloalkyl, halogen, CN, $COOR^2$, $NR^2R^2$, $NO_2$, $SO_2R^2$, $SO_2NR^2R^2$, OH, and phenyl which is unsubstituted or substituted by $C_1$–$C_6$-alkyl, $OC_1$–$C_6$-alkyl, $NR^2R^2$, CN, $CF_3$, $CHF_2$, or halogen, and where the 5- or 6-membered heterocyclic ring may be fused to a phenyl ring;

$R^1$ is $C_3$–$C_6$-cycloalkyl or $C_1$–$C_6$-alkyl which is unsubstituted or substituted by OH or $OC_1$–$C_6$-alkyl;

the radicals $R^2$, which can be identical or different, are H or $C_1$–$C_6$-alkyl which is unsubstituted or substituted by OH, $OC_1$–$C_6$-alkyl or phenyl.

* * * * *